United States Patent
Figadere et al.

(10) Patent No.: US 10,550,115 B2
(45) Date of Patent: Feb. 4, 2020

(54) 1, 4, 8-TRIAZAPHENANTHRENE DERIVATIVES FOR THE TREATMENT OF NEURODEGENERATIVE DISORDERS

(71) Applicants: Institut Du Cerveau et de la Moëlle Epiniere, Paris (FR); Centre National de la Recherche Scientifique (CNRS), Paris (FR); Sorbonne Universite, Paris (FR); Assistance Publique-Hopitaux de Paris, Paris (FR); Institut National de la Sante et de la Recherche Medicale (INSERM), Paris (FR); Universite Paris-SUD, Orsay (FR)

(72) Inventors: Bruno Figadere, Saint Cheron (FR); Laurent Ferrie, Palaiseau (FR); Gael Le Douaron, Verrieres le Buisson (FR); Rita Raisman-Vozari, Paris (FR); Patrick Michel, Paris (FR); Julia Sepulveda, Paris (FR)

(73) Assignees: Institut Du Cerveau et de la Moëlle Epiniere (FR); Centre National de la Recherche Scientifique (CNRS) (FR); Sorbonne Universite (FR); Assistance Publique-Hopitaux de Paris (FR); Institut National de la Sante et de la Recherche Medicale (INSERM) (FR); Universite Paris-SUD (FR)

( * ) Notice: Subject to any disclaimer, the term of this patent is extended or adjusted under 35 U.S.C. 154(b) by 0 days.

(21) Appl. No.: 15/767,053

(22) PCT Filed: Oct. 10, 2016

(86) PCT No.: PCT/EP2016/074235
§ 371 (c)(1),
(2) Date: May 9, 2018

(87) PCT Pub. No.: WO2017/060530
PCT Pub. Date: Apr. 13, 2017

(65) Prior Publication Data
US 2019/0071438 A1 Mar. 7, 2019

(30) Foreign Application Priority Data
Oct. 9, 2015 (FR) .................. 15 59639

(51) Int. Cl.
*C07D 471/04* (2006.01)
*A61P 25/28* (2006.01)
*A61P 25/16* (2006.01)

(52) U.S. Cl.
CPC ............ *C07D 471/04* (2013.01); *A61P 25/16* (2018.01); *A61P 25/28* (2018.01)

(58) Field of Classification Search
CPC .................................................. C07D 471/04

USPC ......................................................... 544/345
See application file for complete search history.

(56) References Cited

U.S. PATENT DOCUMENTS

2011/0118270 A1  5/2011  Schmidt
2014/0113903 A1  4/2014  Ferrie et al.

FOREIGN PATENT DOCUMENTS

WO    2010007179 A1    1/2010
WO    2012131080 A1   10/2012

OTHER PUBLICATIONS

Ganguli et al. Indian Journal of Heterocyclic Chemistry (1994), 3(4), 269-72.*
Akihiro Ohta et al., "Photocyclization of Styrylpyrazines", Chemical and Pharmaceutical Bulletin, Pharmaceutical Society of Japan, JP, vol. 27, No. 11, Jan. 1, 1979 (Jan. 1, 1979), pp. 2596-2600, XP009187945.
Guerreiro et al., "Paraxanthine, the Primary Metabolite of Caffeine, Provides Protection agains Dopaminergic Cell Death via Stimulation of Ryanodine Receptor Channels", Molecular Pharmacology, vol. 74, No. 4, pp. 980-989, Accepted: Jul. 11, 2008.
Huisgen et al., "Beitrage und Deutungsversuche zur reaktionsweise aromatischer Bicyclen", Justus Liebigs Annalene Der Chemie, vol. 559, Jan. 1, 1948 (Jan. 1, 1948), pp. 101-152, XP002752956.
International Search Report for Application No. PCT/EP2016/074235 dated Nov. 7, 2016, 3 pages.
Linsker et al., "Pyridoquinoxalines", Journal of the American Chemical Society, vol. 68, Jan. 1, 1946 (Jan. 1, 1946), pp. 874-876, XP002752955.
Mourlevat et al., "Prevention of Dopaminergic Neuronal Death by Cyclic AMP in Mixed Neuronal/Glial Mesencephalic cultures Requires the Repression of Presumtive Astrocytes", Molecular Pharmacology, vol. 64, No. 3, pp. 578-586, Accepted: May 14, 2003.
Pajouhesh et al., "Medicinal Chemical Properties of Successful Central Nervous System Drugs", The Journal of the American Society for Experimental NeuroTherapeutics, vol. 2, pp. 541-553, Oct. 2005.
Rousseau et al., "The Iron-Binding Protein Lactoferrin Protects Vulnerable Dopamine Neurons from Degeneration by Presersing Mitochondrial Calcium Homeostasis", Molecular Pharmacology, 84: 888-898, Dec. 2013.
Suguru Kondo et al., "Formation of Pyrido(3,2-f)quinoxalines by Reaction of 6-Amino-2,3-dimetylquinoxaline with Aldehydes", Chemical and Pharmaceutical Bulletin, Pharmaceutical Society of Japan, JP, vol. 45, No. 4, Jan. 1, 1997 (Jan. 1, 1997), pp. 722-724, XP009187946.
Toulorge et al., "Neuroprotection of midbrain dopamine neurons by nicotine is gated by cytoplasmic Ca2+", The FASEB Journal / Research Communication, vol. 25, 2563-2573, Aug. 2011.

* cited by examiner

*Primary Examiner* — Kahsay Habte
(74) *Attorney, Agent, or Firm* — Lerner, David, Littenberg, Krumholz & Mentlik, LLP

(57) ABSTRACT

The invention relates to compounds of formula (I), particularly for the use thereof as a medicament, especially in the treatment or prevention of neurogenerative disorders. The invention also relates to the methods for producing said compounds, and to the pharmaceutical compositions containing same.

15 Claims, No Drawings

1,4,8-TRIAZAPHENANTHRENE DERIVATIVES FOR THE TREATMENT OF NEURODEGENERATIVE DISORDERS

The present invention concerns 1,4,8-triazaphenanthrene derivatives, as well as their preparation processes, the pharmaceutical compositions containing them and their use as medicinal products, especially in the treatment of neurodegenerative diseases.

With longer life expectancy, an increasing number of people suffer from neurodegenerative diseases such as Alzheimer's disease or Parkinson's disease.

A neurodegenerative disease is a disease that progressively affects the function of the nervous system, and in particular the brain. It can progress quickly or slowly (several weeks to several years), and often irreversibly. Thus, the function of nerve cells, especially neurons, is deteriorated, which can lead to cell death. Depending on the region of the nervous system affected by the disease, various neurons, and thus various functions, may be affected, such as motor function, language, memory, perception, mood or cognition. The most common neurodegenerative diseases particularly include Alzheimer's disease and Parkinson's disease.

Alzheimer's disease is a brain tissue disease leading to progressive and irreversible loss of cognitive functions, and affects roughly 24 million people worldwide. The first symptom is short-term memory loss (amnesia), then the cognitive deficits extend to the regions of language (aphasia), motor control (apraxia), visual recognition (agnosia) and executive functions (such as decision-making and planning).

Parkinson's disease, too, affects the central nervous system but causes progressive and irreversible motor disorders, with in particular motor control deficits and body tremors.

Today, the medicinal products prescribed for these two diseases are symptomatic and help delay the progression of the disease; none cure the disease, nor even stop its progression, whence the need to find novel, more active chemical entities for the treatment of these neurodegenerative diseases.

The inventors of the present invention have already shown the potential of hybrid compounds having an amino-quinoxaline nucleus in the treatment of neurodegenerative diseases (WO 2012/131080).

The inventors have surprisingly discovered that 1,4,8-triazaphenanthrene derivatives also have neuroprotective activity and are able to cross the blood-brain barrier.

The present invention thus relates to a compound of following formula (I):

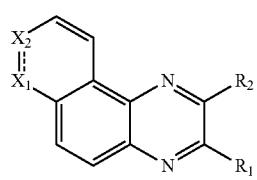

(I)

or a pharmaceutically acceptable salt and/or solvate thereof, a stereoisomer, or a mixture of stereoisomers in any proportions, in particular a mixture of enantiomers, and particularly a racemic mixture, wherein:
   ===== is a single or double bond, preferably a double bond,
   $X_1$ is:
      $NR_{1a}$ when ===== is a single bond, and
      $N$ when ===== is a double bond,
   $X_2$ is:
      $CR_{2a}R_{2b}$ when ===== is a single bond, and
      $CR_{2c}$ when ===== is a double bond,
   $R_1$ and $R_2$ are each independently a hydrogen atom; a halogen atom such as a chlorine, bromine or fluorine atom; a linear or branched, saturated or unsaturated hydrocarbon chain having from 1 to 10, preferably 1 to 6 carbon atoms; an optionally substituted aryl; or an optionally substituted heteroaryl,
   $R_{1a}$ and $R_{2c}$ are each independently a hydrogen atom or a $(C_1\text{-}C_6)$alkyl group, and
   $R_{2a}$ and $R_{2b}$ are each independently a $(C_1\text{-}C_6)$alkyl group.

The compound of formula (I) can be in the form of one or more stereoisomers more particularly when $X_1$=$CR_{2a}R_{2b}$ with $R_{2a}$ and $R_{2b}$ being two different groups and/or when at least one group among $R_1$, $R_2$, $R_{1a}$, $R_{2a}$, $R_{2b}$ and $R_{2c}$ is a chiral group.

According to a particular embodiment, the compound of formula (I) is not:
pyrido[3,2-f]quinoxaline,
2,3-dimethyl-pyrido[3,2-f]quinoxaline,
2,3,8-trimethyl-pyrido[3,2-f]quinoxaline, and
2,3-diphenyl-pyrido[3,2-f]quinoxaline,
compounds described in the literature (Linsker et al. *J. Am. Chem. Soc.* 1946, 68, 874-876; Kondo et al. *Chem. Pharm. Bull.* 1997, 45(4), 722-724; Ohta et al. *Chem. Pharm. Bull.* 1979, 27(11), 2596-2600; and Huisgen *Justus Liebigs Annalene der Chemie* 1948, 559, 101-152), in chemical synthesis articles, no biological activity being reported for these compounds.

In the present invention, the term "pharmaceutically acceptable" is intended to mean that which is useful in the preparation of a pharmaceutical composition which is generally safe, nontoxic and neither biologically nor otherwise undesirable and which is acceptable for both veterinary and human pharmaceutical use.

The term "pharmaceutically acceptable salt" of a compound is intended to mean in the present invention salts which are pharmaceutically acceptable, as defined herein, and which have the desired pharmacological activity of the parent compound. Such salts include:
(1) the acid addition salts formed with inorganic acids such as hydrochloric acid, hydrobromic acid, sulphuric acid, nitric acid, phosphoric acid and the like; or formed with organic acids such as acetic acid, benzenesulfonic acid, benzoic acid, camphorsulphonic acid, citric acid, ethanesulphonic acid, fumaric acid, glucoheptonic acid, gluconic acid, glutamic acid, glycolic acid, hydroxynaphthoic acid, 2-hydroxyethanesulphonic acid, lactic acid, maleic acid, malic acid, mandelic acid, methanesulphonic acid, muconic acid, 2-naphthalene-sulphonic acid, propionic acid, salicylic acid, succinic acid, dibenzoyl-L-tartaric acid, tartaric acid, p-toluenesulphonic acid, trimethylacetic acid, trifluoroacetic acid and the like; and
(2) the salts formed when an acidic proton present in the parent compound is either replaced by a metal ion, e.g., an alkali metal ion (e.g., $Na^+$, $K^+$ or $Li^+$), an alkaline-earth metal ion (like $Ca^{2+}$ or $Mg^{2+}$) or an aluminium ion; or coordinates with an organic or inorganic base. The acceptable organic bases include diethanolamine, ethanolamine, N-methylglucamine, triethanolamine, tromethamine and the like. The acceptable inorganic bases include aluminium hydroxide, calcium hydroxide, potassium hydroxide, sodium carbonate and sodium hydroxide.

Solvates acceptable for pharmaceutical use of the compounds of the present invention include conventional solvates such as those formed, during the last step of the process for preparing the compounds of the invention, with the reaction solvent(s). By way of example, mention may be made of the solvates formed with water (commonly called hydrates) or with ethanol.

The term "($C_1$-$C_6$)alkyl" group is understood to mean, within the meaning of the present invention, a saturated, linear or branched hydrocarbon chain having 1 to 6, preferably 1 to 4, carbon atoms. By way of example, mention may be made of methyl, ethyl, propyl, isopropyl, butyl, isobutyl, sec-butyl, tert-butyl, pentyl or hexyl groups.

The term "($C_1$-$C_6$)alkoxy" group is understood to mean, within the meaning of the present invention, a ($C_1$-$C_6$)alkyl group as defined above, attached to the rest of the molecule via an oxygen atom. By way of example, mention may be made of methoxy, ethoxy, propoxy, isopropoxy, butoxy or tert-butoxy groups.

The term "($C_2$-$C_6$)alkynyl" group is understood to mean, within the meaning of the present invention, a linear or branched hydrocarbon chain having at least one triple bond and having 2 to 6 carbon atoms. The ($C_2$-$C_6$)alkynyl group will have advantageously one and only one triple bond. By way of example, mention may be made of ethynyl or propynyl groups.

The term "aryl" group is understood to mean, within the meaning of the present invention, an aromatic hydrocarbon group having preferably from 6 to 10 carbon atoms and having one or more fused rings. It will be advantageously a phenyl or naphthyl group.

When the aryl group is substituted, it may advantageously be substituted by one or more groups selected from a halogen atom, ($C_1$-$C_6$)alkyl, ($C_1$-$C_6$)alkoxy, aryl, $N_3$, $NO_2$, OH, $NH_2$, and —NH—(($C_1$-$C_6$)alkyl); preferably selected from a halogen atom, ($C_1$-$C_6$)alkyl, ($C_1$-$C_6$)alkoxy, OH and aryl.

The term "heteroaryl" is understood to mean, within the meaning of the present invention, an aromatic group having one or more, particularly 1 or 2, fused hydrocarbon rings, wherein one or more carbon atoms, advantageously 1 to 4 and even more advantageously 1 or 2, are each replaced by a heteroatom selected from sulphur, nitrogen and oxygen atoms and wherein each ring has advantageously 5 to 7 members, preferably 5 or 6 members. Advantageously, it will be an aromatic group having 1 or 2 fused hydrocarbon rings, each ring having 5 or 6 members, wherein 1 or 2 carbon atoms are each replaced by a heteroatom selected from sulphur, nitrogen and oxygen atoms, preferably selected from nitrogen and oxygen atoms, such as nitrogen. Examples of heteroaryl groups are furyl, thienyl, pyrrolyl, isoxazolyl, thiazolyl, isothiazolyl, imidazolyl, pyrazolyl, oxadiazolyl, thiadiazolyl, triazolyl, tetrazolyl, pyridyl, pyridazinyl, pyrimidinyl, pyrazinyl, triazinyl, quinolyl, quinoxalyl or indyl groups. It will be particularly a pyridyl, quinoxalyl or quinolyl group, in particular pyridyl or quinolyl.

When the heteroaryl group is substituted, it may advantageously be substituted by one or more groups selected from a halogen atom, ($C_1$-$C_6$)alkyl, ($C_1$-$C_6$)alkoxy, aryl, $N_3$, $NO_2$, OH, $NH_2$, and —NH—(($C_1$-$C_6$)alkyl); preferably selected from a halogen atom, ($C_1$-$C_6$)alkyl, ($C_1$-$C_6$)alkoxy, OH and aryl.

The term "halogen atom" is understood to mean, within the meaning of the present invention, fluorine, bromine, chlorine and iodine atoms, preferably fluorine, chlorine and bromine.

The term "unsaturated" is understood to mean, within the meaning of the present invention, that the hydrocarbon chain can have one or more unsaturation(s), advantageously one.

The term "unsaturation" is understood to mean, within the meaning of the present invention, a double or triple carbon-carbon bond (C=C or C≡C).

The term "stereoisomer" is understood to mean, within the meaning of the present invention, a geometric isomer or an optical isomer.

Geometric isomers result from the different positions of the substituents on a double bond, which can thus have a Z or E configuration.

Optical isomers result in particular from the different position in space of the substituents on a carbon atom having 4 different substituents. This carbon atom thus constitutes a chiral or asymmetric centre. Optical isomers include diastereoisomers and enantiomers. Optical isomers that are mirror images of each other but are non-superimposable are called "enantiomers". Optical isomers that are non-superimposable and that are not mirror images of each other are called "diastereoisomers".

A mixture containing equal amounts of two individual enantiomer forms of opposite chirality is called a "racemic mixture".

The term "chiral group" is understood to mean, within the meaning of the present invention, a group which is non-superimposable on its mirror image. Such a chiral group may include in particular a chiral carbon atom, i.e., a carbon atom substituted by four different substituents (including hydrogen).

According to a preferred embodiment, ====== is a double bond. Consequently, $X_1$ is N and $X_2$ is a $CR_{2c}$ group in this preferred embodiment. $R_{2c}$ will be advantageously a hydrogen atom. A compound of the present invention will thus be advantageously a compound of following formula (Ia):

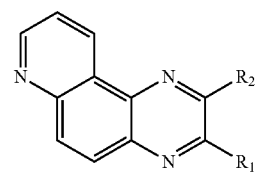

(Ia)

or a pharmaceutically acceptable salt and/or solvate thereof, a stereoisomer, or a mixture of stereoisomers in any proportions, in particular a mixture of enantiomers, and particularly a racemic mixture, wherein $R_1$ and $R_2$ are as defined above or below.

In the definition of $R_1$ and $R_2$, the term "linear or branched, saturated or unsaturated hydrocarbon chain having from 1 to 10, preferably 1 to 6 carbon atoms" will mean more particularly:

a linear or branched, saturated hydrocarbon chain having from 1 to 10, preferably 1 to 6 carbon atoms, and more particularly a ($C_1$-$C_6$)alkyl group as defined above, or a linear or branched, unsaturated hydrocarbon chain having from 1 to 10, preferably 1 to 6 carbon atoms and having at least one triple bond, and advantageously having one and only one triple bond as unsaturation, and more particularly a ($C_2$-$C_6$)alkynyl group as defined above.

Advantageously, $R_1$ and $R_2$ are each independently:
a hydrogen atom,
a halogen atom such as chlorine, fluorine and bromine,
a linear or branched, saturated or unsaturated hydrocarbon chain having from 1 to 10, preferably 1 to 6 carbon atoms,
an aryl optionally substituted by one or more groups selected from a halogen atom, ($C_1$-$C_6$)alkyl, ($C_1$-$C_6$)alkoxy, aryl, $N_3$, $NO_2$, OH, $NH_2$, and —NH—(($C_1$-$C_6$)alkyl); preferably selected from a halogen atom, ($C_1$-$C_6$)alkyl, ($C_1$-$C_6$)alkoxy, OH and aryl; particularly selected from ($C_1$-$C_6$)alkoxy and OH, or
a heteroaryl optionally substituted by one or more groups selected from a halogen atom, ($C_1$-$C_6$)alkyl, ($C_1$-$C_6$)alkoxy, aryl, $N_3$, $NO_2$, OH, $NH_2$, and —NH—(($C_1$-$C_6$)alkyl); preferably selected from a halogen atom, ($C_1$-$C_6$)alkyl, ($C_1$-$C_6$)alkoxy, OH and aryl; particularly selected from ($C_1$-$C_6$)alkoxy and OH.

In particular, $R_1$ and $R_2$ can be each independently:
a hydrogen atom,
a halogen atom such as chlorine, fluorine and bromine,
a ($C_1$-$C_6$)alkyl,
a ($C_2$-$C_6$)alkynyl, advantageously having one and only one triple bond,
an aryl optionally substituted by one or more groups selected from a halogen atom, ($C_1$-$C_6$)alkyl, ($C_1$-$C_6$)alkoxy, aryl, $N_3$, $NO_2$, OH, $NH_2$, and —NH—(($C_1$-$C_6$)alkyl); preferably selected from a halogen atom, ($C_1$-$C_6$)alkyl, ($C_1$-$C_6$)alkoxy, OH and aryl; particularly selected from ($C_1$-$C_6$)alkoxy and OH, or
a heteroaryl optionally substituted by one or more groups selected from a halogen atom, ($C_1$-$C_6$)alkyl, ($C_1$-$C_6$)alkoxy, aryl, $N_3$, $NO_2$, OH, $NH_2$, and —NH—(($C_1$-$C_6$)alkyl); preferably selected from a halogen atom, ($C_1$-$C_6$)alkyl, ($C_1$-$C_6$)alkoxy, OH and aryl; particularly selected from ($C_1$-$C_6$)alkoxy and OH.

Preferably, $R_1$ and $R_2$ will be each independently:
a hydrogen atom,
a ($C_1$-$C_6$)alkyl,
a ($C_2$-$C_6$)alkynyl, advantageously having one and only one triple bond,
an aryl optionally substituted by one or more groups selected from a halogen atom, ($C_1$-$C_6$)alkyl, ($C_1$-$C_6$)alkoxy, aryl, $N_3$, $NO_2$, OH, $NH_2$, and —NH—(($C_1$-$C_6$)alkyl); preferably selected from a halogen atom, ($C_1$-$C_6$)alkyl, ($C_1$-$C_6$)alkoxy, OH and aryl; particularly selected from ($C_1$-$C_6$)alkoxy and OH, or
a heteroaryl optionally substituted by one or more groups selected from a halogen atom, ($C_1$-$C_6$)alkyl, ($C_1$-$C_6$)alkoxy, aryl, $N_3$, $NO_2$, OH, $NH_2$, and —NH—(($C_1$-$C_6$)alkyl); preferably selected from a halogen atom, ($C_1$-$C_6$)alkyl, ($C_1$-$C_6$)alkoxy, OH and aryl; particularly selected from ($C_1$-$C_6$)alkoxy and OH.

Advantageously, $R_1$ and $R_2$ are each independently a hydrogen atom; a ($C_1$-$C_6$)alkyl group; or an optionally substituted aryl or heteroaryl group, particularly optionally substituted by one or more groups selected from a halogen atom, ($C_1$-$C_6$)alkyl, ($C_1$-$C_6$)alkoxy, aryl, $N_3$, $NO_2$, OH, $NH_2$, and —NH—(($C_1$-$C_6$)alkyl); preferably selected from a halogen atom, ($C_1$-$C_6$)alkyl, ($C_1$-$C_6$)alkoxy, OH and aryl; particularly selected from ($C_1$-$C_6$)alkoxy and OH.

In particular, $R_1$ and $R_2$ can be each independently a hydrogen atom; a ($C_1$-$C_6$)alkyl group; or a phenyl, naphthyl, pyridyl, quinoxalyl or quinolyl group, particularly phenyl, naphthyl, pyridyl or quinolyl, optionally substituted, particularly by one or more groups selected from a halogen atom, ($C_1$-$C_6$)alkyl, ($C_1$-$C_6$)alkoxy, aryl, $N_3$, $NO_2$, OH, $NH_2$, and —NH—(($C_1$-$C_6$)alkyl); preferably selected from a halogen atom, ($C_1$-$C_6$)alkyl, ($C_1$-$C_6$)alkoxy, OH and aryl; particularly selected from ($C_1$-$C_6$)alkoxy and OH.

According to a particular embodiment of the invention, $R_1$ will be a hydrogen atom or a ($C_1$-$C_6$)alkyl group such as methyl, particularly a hydrogen atom.

According to another particular embodiment of the invention, $R_2$ will be an aryl or heteroaryl group, preferably aryl, optionally substituted, particularly by one or more groups selected from a halogen atom, ($C_1$-$C_6$)alkyl, ($C_1$-$C_6$)alkoxy, aryl, $N_3$, $NO_2$, OH, $NH_2$, and —NH—(($C_1$-$C_6$)alkyl); preferably selected from a halogen atom, ($C_1$-$C_6$)alkyl, ($C_1$-$C_6$)alkoxy, OH and aryl; particularly selected from ($C_1$-$C_6$)alkoxy and OH. $R_2$ can be in particular a phenyl, naphthyl, pyridyl, quinoxalyl or quinolyl group, particularly phenyl, naphthyl, pyridyl or quinolyl, preferably phenyl, optionally substituted, particularly by one or more groups selected from a halogen atom, ($C_1$-$C_6$)alkyl, ($C_1$-$C_6$)alkoxy, aryl, $N_3$, $NO_2$, OH, $NH_2$, and —NH—(($C_1$-$C_6$)alkyl); preferably selected from a halogen atom, ($C_1$-$C_6$)alkyl, ($C_1$-$C_6$)alkoxy, OH and aryl; particularly selected from ($C_1$-$C_6$)alkoxy and OH.

According to a preferred embodiment of the invention, $R_1$ will be a hydrogen atom or a ($C_1$-$C_6$)alkyl group such as methyl, particularly a hydrogen atom, and $R_2$ will be an aryl or heteroaryl group, preferably aryl, optionally substituted, particularly by one or more groups selected from a halogen atom, ($C_1$-$C_6$)alkyl, ($C_1$-$C_6$)alkoxy, aryl, $N_3$, $NO_2$, OH, $NH_2$, and —NH—(($C_1$-$C_6$)alkyl); preferably selected from a halogen atom, ($C_1$-$C_6$)alkyl, ($C_1$-$C_6$)alkoxy, OH and aryl; particularly selected from ($C_1$-$C_6$)alkoxy and OH. $R_2$ can be in particular a phenyl, naphthyl, pyridyl, quinoxalyl or quinolyl group, particularly phenyl, naphthyl, pyridyl or quinolyl, preferably phenyl, optionally substituted, particularly by one or more groups selected from a halogen atom, ($C_1$-$C_6$)alkyl, ($C_1$-$C_6$)alkoxy, aryl, $N_3$, $NO_2$, OH, $NH_2$, and —NH—(($C_1$-$C_6$)alkyl); preferably selected from a halogen atom, ($C_1$-$C_6$)alkyl, ($C_1$-$C_6$)alkoxy, OH and aryl; particularly selected from ($C_1$-$C_6$)alkoxy and OH.

In the definitions of $R_1$ and $R_2$ above, the ($C_1$-$C_6$)alkyl group can be more particularly a methyl, n-butyl, s-butyl, t-butyl or n-hexyl group, such as methyl; the ($C_2$-$C_6$)alkynyl group can be more particularly an ethynyl group; the optionally substituted aryl group can be more particularly a phenyl or naphthyl group, preferably phenyl, optionally substituted, such as a phenyl, 1-naphthyl, 2-naphthyl, m-hydroxyphenyl, m-methoxyphenyl, p-methoxyphenyl, p-chlorophenyl, p-fluorophenyl, p-methylphenyl, 3,4-dimethoxyphenyl, 3,4,5-trimethoxyphenyl, 3,4-dichlorophenyl, or biphenyl group; the optionally substituted heteroaryl group can be more particularly a pyridyl, quinoxalyl or quinolyl group, particularly pyridyl or quinolyl, optionally substituted and particularly unsubstituted, such as a 3-pyridyl or 3-quinolyl group.

The compounds of formula (I) can particularly be selected from the following compounds:

Iac

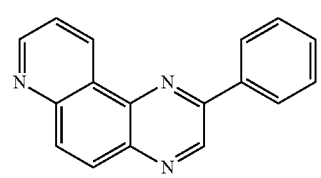

| | |
|---|---|
| Iaf | Iaj |
| Iaa | Iak |
| Iag | Ibn |
| Iad | Ibl |
| Iam | Ibf |
| Iae | Ibo |
| Iah | Ibp |
| Iai | Ibh |

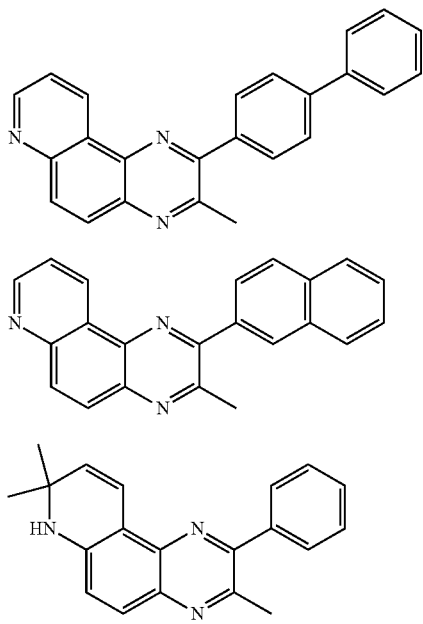

and the pharmaceutically acceptable salts and/or solvates thereof.

The present invention also relates to a compound of formula (I) as defined above, for use as a medicinal product, especially as a neurotrophic or neuroprotective medicinal product, and more particularly for use in the treatment or prevention of a neurodegenerative disease.

The present invention also relates to the use of a compound of formula (I) as defined above for the manufacture of a medicinal product, especially a neurotrophic or neuroprotective medicinal product, and more particularly for the manufacture of a medicinal product intended for the treatment or prevention of a neurodegenerative disease.

The present invention also relates to a method for treating or preventing a neurodegenerative disease comprising administering an effective amount of a compound of formula (I) as defined above to a patient in need thereof.

The neurodegenerative disease can be more particularly Alzheimer's disease, Parkinson's disease, multiple sclerosis or amyotrophic lateral sclerosis (ALS), also called Charcot's disease, and in particular Parkinson's disease.

The present invention also relates to a pharmaceutical composition comprising at least one compound of formula (I) as defined above and a pharmaceutically acceptable vehicle.

The term "pharmaceutical composition" is intended to mean, within the meaning of the present invention, a composition having therapeutic or prophylactic properties with regard to diseases, such as neurodegenerative diseases in the present case, intended to be administered to an animal, especially a mammal such as man.

The pharmaceutical compositions according to the invention can be formulated for parenteral (e.g., subcutaneous, intraperitoneal, intramuscular, intravenous, intracranial, intrathecal, etc.), oral, sublingual, transdermal, local or rectal administration, intended for mammals, including man. Dosing varies according to the treatment and the affection concerned.

In the pharmaceutical compositions of the present invention, the active ingredient can be administered in unit dosage forms, mixed with conventional pharmaceutical excipients, to animals or to human beings.

The suitable oral unit dosage forms include tablets, capsules, powders, granules and oral solutions or suspensions, and parenteral dosage forms, especially intraperitoneal.

When a solid composition is prepared in tablet form, the main active ingredient is mixed with a pharmaceutical vehicle such as gelatin, starch, lactose, magnesium stearate, talc, gum arabic, or the like. The tablets can be coated with sucrose or other suitable materials or they can be treated so that they have extended or delayed activity and that they continuously release a predetermined amount of active ingredient.

A capsule preparation is obtained by mixing the active ingredient with a diluent and pouring the mixture obtained into hard or soft capsules.

A preparation in syrup or elixir form can contain the active ingredient together with a sweetener, an antiseptic, as well as a taste enhancer and a suitable dye.

Water-dispersible powders or granules can contain the active ingredient mixed with dispersants or wetting agents, or suspension agents, and with flavour correctors or sweeteners.

For parenteral administration, use is made of aqueous suspensions, isotonic saline solutions or sterile injectable solutions that contain pharmacologically compatible dispersants and/or wetting agents.

The active ingredient can be also formulated as microcapsules, optionally with one or more additional carriers.

The compounds of the invention can be used in doses ranging between 0.01 mg and 1000 mg per day, given in a single dose once daily or administered in several doses throughout the day, for example twice daily in equal doses. The dose administered per day is advantageously between 5 mg and 500 mg, even more advantageously between 10 mg and 200 mg. It may be necessary to use doses outside these ranges, which persons skilled in the art will be able to determine.

According to a particular embodiment, the pharmaceutical composition as defined above may further comprise another active ingredient, particularly useful in the treatment or prevention of neurodegenerative diseases, and advantageously selected from acetylcholinesterase inhibitors such as donepezil, galantamine, rivastigmine, memantine and tacrine; monoamine oxidase inhibitors such as selegiline or rasagiline; catecholamine O-methyltransferase inhibitors such as entacapone; glutamatergic inhibitors such as amantadine and baclofen; cholinergic agonists such as sabcomeline; dopaminergic agonists such as pergolide, cabergoline, ropinirole and pramipexole; neurotransmitter analogues or precursors such as L-3,4-dihydroxyphenylalanine; and anticholinergics such as trihexyphenidyl and tropatepine.

The present invention also relates to a pharmaceutical composition according to the invention for use as a neurotrophic or neuroprotective medicinal product, and more particularly for use in the treatment or prevention of a neurodegenerative disease, particularly as previously defined.

The present invention also concerns the use of a pharmaceutical composition according to the invention for the manufacture of a neurotrophic or neuroprotective medicinal product, and more particularly for the manufacture of a medicinal product intended for the treatment or prevention of a neurodegenerative disease, particularly as previously defined.

The present invention also concerns a method for treating or preventing a neurodegenerative disease, in particular as previously defined, comprising administering an effective amount of a pharmaceutical composition according to the invention to a patient in need thereof.

The present invention also relates to a first process for preparing a compound of formula (I) as defined above comprising the following successive steps:
(a1) coupling between an amino-quinoxaline of following formula (II):

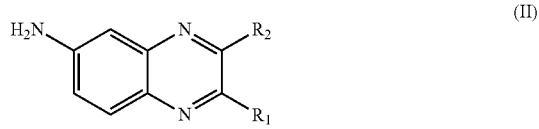

wherein $R_1$ and $R_2$ are as previously defined,
with a propargyl halide of formula CH≡C—CHR$_{2c}$Hal or CH≡C—CR$_{2a}$R$_{2b}$Hal wherein $R_{2a}$, $R_{2b}$ and $R_{2c}$ are as previously defined and Hal is a halogen atom such as Cl, Br or I, particularly Br or Cl,
to give a compound of following formula (IIIa) or (IIIb):

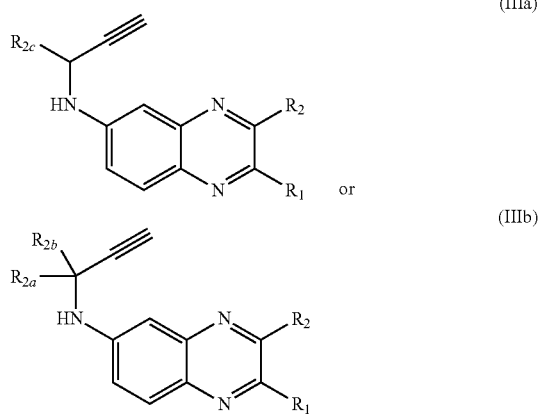

wherein $R_1$, $R_2$, $R_{2a}$, $R_{2b}$ and $R_{2c}$ are as previously defined,
(b1) cycloisomerization of the compound of formula (IIIa) or (IIIb) obtained in the preceding step and aromatization when ===== is a double bond to give a compound of formula (I), and
(c1) optionally salification and/or solvation of the compound of formula (I) obtained in the preceding step to give a pharmaceutically acceptable salt and/or solvate of the compound of formula (I).

Step (a1):

The starting products used for this step (aminoquinoxaline of formula (II)) are commercially available or can be easily prepared by methods well-known to persons skilled in the art. Their synthesis is notably described in the preceding international applications WO 2010/007179 and WO 2012/131080. Synthesis processes are also illustrated in the experimental section below.

This coupling reaction will be advantageously performed in the presence of a base such as $K_2CO_3$ or $K_3PO_4$, and particularly an iodide such as KI, NaI or nBu$_4$NI.

This reaction can be advantageously performed in a solvent such as dimethylformamide (DMF), dioxane, NMP (N-methyl pyrrolidinone), DMSO (dimethylsulphoxide), DMPU (1,3-dimethyl-3,4,5,6-tetrahydro-2(1H)-pyrimidinone), HMPA (hexamethylphosphoramide), DMA (dimethylacetamide) or a mixture thereof, and in particular DMF, notably at a temperature of 50 to 140° C., notably of about 80° C.

Step (b1):

The cycloisomerization reaction will be advantageously performed in the presence of a catalyst such as a copper (I) derivative (e.g., CuCl, Cu$_2$O, CuOTf, CuPF$_6$ or CuBF$_4$) or a silver salt (e.g., AgNO$_3$, Ag$_2$CO$_3$, AgF, AgPF$_6$, AgOTf, AgBF$_4$ or CF$_3$C(O)OAg). The catalyst will be more particularly CuCl.

This reaction can be advantageously performed in a solvent such as dimethylsulphoxide (DMSO), chloroform, toluene, DMF, dioxane, NMP, DMPU, HMPA, DMA or a mixture thereof, and in particular DMSO or toluene, notably at a temperature of 70 to 160° C., notably of about 120° C.

This cycloisomerization reaction is accompanied spontaneously by aromatization of the tricyclic system when step (b1) is performed from a compound of formula (IIIa) to give a derivative of 1,4,8-triazaphenanthrene type.

Step (c1):

The salification step can be performed under conditions well-known to persons skilled in the art, in the presence of a pharmaceutically acceptable acid or base, notably as previously defined.

When the compound is in a solvated form, this solvation generally takes place in the last step of the process, the solvent of the solvated form being in this case the solvent of the reaction medium.

The present invention also relates to a second process for preparing a compound of formula (I) above wherein at least one of $R_1$ and $R_2$ is a linear or branched, saturated or unsaturated hydrocarbon chain having from 1 to 10 carbon atoms; an optionally substituted aryl; or an optionally substituted heteroaryl, comprising the following successive steps:
(a2) coupling of a compound of formula (I) according to the invention wherein at least one of $R_1$ and $R_2$ is a halogen atom, such as Cl, Br or I, particularly Cl, with a boronic acid derivative of formula $R_3$—B($R_4$)$_2$ or $R_3$—BF$_3^-$K$^+$ wherein $R_3$ is a linear or branched, saturated or unsaturated hydrocarbon chain having from 1 to 10 carbon atoms; an optionally substituted aryl; or an optionally substituted heteroaryl, and $R_4$ is a ($C_1$-$C_6$) alkyl, OH or ($C_1$-$C_6$)alkoxy group, or with a zinc derivative of formula $R_3$—Zn-Hal wherein $R_3$ is as defined above and Hal is a halogen atom such as Cl, Br or I, particularly Cl,
or with a stannane derivative of formula $R_3$—SnA$_1$A$_2$A$_3$ wherein $R_3$ is as defined above and A$_1$, A$_2$ and A$_3$, which can be identical or different, are each a ($C_1$-$C_6$)alkyl group,
or with a magnesium derivative of formula $R_3$—Mg-Hal wherein $R_3$ is as defined above and Hal is a halogen atom such as Cl, Br or I, particularly Br, or with a silicon derivative of formula $R_3$—SiMe$_2$OH, $R_3$—SiF$_3$ or $R_3$—Si(OA$_1$)(OA$_2$)(OA$_3$) wherein $R_3$, A$_1$, A$_2$ and A$_3$ are as defined above, or with an alkyne of formula R'—C≡CH wherein R' is a protecting group or a linear or branched, saturated or unsaturated hydrocarbon chain having from 1 to 8 carbon atoms,
(b2) when step (a2) was performed with an alkyne of formula R'—C≡CH wherein R' is a protecting group, deprotection of the protecting group of the alkyne function, and (c2) optionally salification and/or solvation of the compound of formula (I) obtained in the preceding step to give a pharmaceutically acceptable salt and/or solvate of the compound of formula (I).

Step (a2):

Coupling with a Boronic Acid of Formula $R_3$—$B(R_4)_2$ or $R_3$—$BF_3^-K^+$.

This coupling can be performed under the Suzuki reaction conditions well-known to persons skilled in the art.

This coupling reaction will thus advantageously be performed in the presence of a palladium catalyst such as $Pd(PPh_3)_4$, $Pd(OAc)_2$, $PdCl_2(dppf)$ or $PdCl_2(PPh_3)_2$, particularly $PdCl_2(PPh_3)_2$.

It can be performed in the presence of a base such as $K_2CO_3$, $K_3PO_4$, $Na_2CO_3$, $Cs_2CO_3$, KOH, CsOH or NaOH, particularly $K_2CO_3$.

This reaction can be advantageously performed in a solvent selected from dioxane, water and mixtures thereof, more particularly in a water/dioxane mixture, in particular at reflux.

The boronic acid derivative used can be more particularly a boronic acid of formula $R_3$—$B(OH)_2$.

Coupling with a Zinc Derivative of Formula $R_3$—Zn-Hal:

This coupling can be performed under the Negishi reaction conditions well-known to persons skilled in the art.

This coupling reaction will thus advantageously be performed in the presence of a palladium catalyst such as $Pd(PPh_3)_4$. A nickel catalyst can also be considered.

This reaction can be advantageously performed in a solvent such as tetrahydrofuran (THF).

Coupling with a Stannane Derivative of Formula $R_3$—$SnA_1A_2A_3$:

This coupling can be performed under the Stille reaction conditions well-known to persons skilled in the art.

This coupling reaction will thus advantageously be performed in the presence of a palladium catalyst such as $Pd(PPh_3)_4$. The addition of copper salts such as CuTC, CuDPP, or CuCl can be used to facilitate the reaction.

$A_1$, $A_2$ and $A_3$ will be advantageously identical, and will be particularly Me or Bu, particularly Bu.

Coupling with a Magnesium Derivative of Formula $R_3$—Mg-Hal:

This coupling can be performed under the Kumada reaction conditions well-known to persons skilled in the art.

This coupling reaction will thus advantageously be performed in the presence of a palladium catalyst such as $Pd(PPh_3)_4$ or $PdCl_2(dppf)$ or of a nickel catalyst such as $Ni(acac)_2$, $NiCl_2(dppp)$, $NiCl_2(dppe)$ or $NiCl_2(dppb)$.

Coupling with a Silicon Derivative of Formula $R_3$—$SiMe_2OH$, $R_3$—$SiF_3$ or $R_3$—$Si(OA_1)(OA_2)(OA_3)$:

This coupling can be performed under the Hiyama reaction conditions well-known to persons skilled in the art.

This coupling reaction will thus advantageously be performed in the presence of a palladium catalyst such as $PdCl_2$, $Pd_2dba_3$, $Pd(OAc)_2$, $Pd(PPh_3)_4$ or $PdCl_2(dppf)$ or of a nickel catalyst such as $Ni(acac)_2$, $NiCl_2$ (dppp), $NiCl_2$ (dppe), $NiCl_2$ (dppb), $NiBr_2$.diglyme or $NiCl_2$.glyme.

This coupling reaction will be also advantageously performed in the presence of a fluoride source such as TBAF (tetra-n-butylammonium fluoride), TASF (tris(dimethylamino)sulfonium difluorotrimethylsilicate) or CsF, or of hydroxide such as NaOH or KOH $A_1$, $A_2$ and $A_3$ will be advantageously identical, and will be notably Me or Et.

Coupling with an Alkyne of Formula R'—C≡CH:

This coupling can be performed under the Sonogashira reaction conditions well-known to persons skilled in the art.

This coupling reaction will thus advantageously be performed in the presence of a palladium catalyst such as $Pd(PPh_3)_4$ or $PdCl_2(PPh_3)_2$, particularly $PdCl_2(PPh_3)_2$, and of a copper (I) salt such as CuI or CuBr, particularly CuI.

It can be performed in the presence of a base such as a tertiary or secondary amine, for example $NHEt_2$, $NEt_3$ or $NEt(iPr)_2$, particularly $NEt_3$.

This reaction can be advantageously performed in a solvent selected from THF (tetrahydrofuran), acetonitrile, ethyl acetate and mixtures thereof, more particularly in THF, particularly at reflux.

The coupling of step (a2) will be advantageously performed by a Suzuki or Sonogashira reaction.

Step (b2):

The protecting group of the alkyne function can be a silyl group such as $SiA_4A_5A_6$ where $A_4$, $A_5$ and $A_6$ are each independently a $(C_1-C_6)$alkyl group. It can be more particularly a trimethylsilyl (TMS) group.

It can be deprotected under conditions well-known to persons skilled in the art, and notably in the presence of a base such as $K_2CO_3$ in methanol as solvent or in the presence of a fluoride source such as TBAF in THF as solvent. Such a deprotection can be performed at room temperature or by heating to a temperature ranging up to the reflux temperature of the solvent.

A compound of formula (I) with at least one of $R_1$ and $R_2$ being a —C≡CH group is thus obtained.

Step (c2): See Preceding Step (c1).

The compound obtained by one of the two processes above can be separated from the reaction medium by methods well-known to persons skilled in the art, for instance by extraction, evaporation of the solvent or by precipitation and filtration.

It can also be purified if necessary by techniques well-known to persons skilled in the art, such as by recrystallization if the compound is crystalline, by distillation, by column chromatography on silica gel or alumina, or by high-performance liquid chromatography (HPLC).

The present invention will be better understood in the light of the following non-limiting examples.

EXAMPLES

The following abbreviations have been used in this section.

AMP: Adenosine 3',5'-monophosphate
db-cAMP: Dibutyryl cyclic adenosine 3',5'-monophosphate
BBB: Blood-brain barrier
DCM: Dichloromethane
DMSO: Dimethylsulphoxide
equiv.: Equivalent
ESI: Electrospray ionization
HPLC: High-performance liquid chromatography
HPLC-: High-performance liquid chromatography-tandem mass spectrometry
MS/MS
IR: Infrared
MRM: Multiple reaction monitoring
MS: Mass spectrum
NMR: Nuclear magnetic resonance
THF: Tetrahydrofuran
UHPLC: Ultra-high-performance liquid chromatography
UV: Ultraviolet The compounds of the invention were named in the form Ixy (when ----- is a single bond and $R_{2c}$ =H) or Xxy (when ----- is a double bond and $R_{2a}$=$R_{2b}$=Me) where:

the first suffix x corresponds to $R_2$,
the second suffix y corresponds to $R_1$,
with as suffixes: a=H, b=Me, c=Ph, d=Cl, e=m-hydroxyphenyl, f=3,4,5-trimethoxyphenyl, g=3-pyridyl, h=p-fluorophenyl, i=1-naphthyl, j=2-naphthyl, k=1-ethynyl, l=p-methoxyphenyl, m=3-quinolyl, n=p-methylphenyl, o=p-chlorophenyl, p=3,4-dichlorophenyl, q=biphenyl.

The same nomenclature was used for the synthetic intermediates of formula (II) or (IIIa) (with $R_{2c}$=H) in the form IIxy and IIIxy, respectively.

Synthesis of the aminoquinoxalines of formula (II) used in the examples is either described below or described in WO 2010/007179 or WO 2012/131080.

I. Synthesis of the Compounds of the Invention

Example 1: Synthesis of Compound Ibl

Step 1:
To a solution of compound IIbl (343 mg, 1.29 mmol, 1 equiv.) in anhydrous dimethylformamide are added 178 mg of $K_2CO_3$ (1.29 mmol, 1 equiv.), 214 mg of KI (1.29 mmol, 1 equiv.) and 0.288 mL of propargyl bromide (1.7 mmol, 2 equiv., 80% in toluene). The reaction mixture is then heated to 80° C. for 24 h. After cooling, the reaction mixture is hydrolysed by a saturated solution of $K_2CO_3$, then extracted 3 times with ethyl acetate. The organic phases are combined, washed with a saturated solution of NaCl, dried over $Na_2SO_4$, filtered and then concentrated under reduced pressure. Purification by chromatography on silica gel in a cyclohexane:ethyl acetate mixture in 7:3 then 6:4 proportions made it possible to obtain compound IIIbl (71%, 280.0 mg) as well as the disubstituted compound (14%, 64.1 mg). $^1$H NMR (400 MHz, CDCl$_3$) δ ppm: 2.24 (t, J=2.4 Hz, 1H), 2.70 (s, 3H), 3.86 (s, 3H), 4.03 (d, J=2.4 Hz, 2H), 4.44 (brs, 1H, NH), 7.02 (d, J=8.7 Hz, 2H), 7.09 (dd, J=8.7, 2.5 Hz, 1H), 7.12 (d, J=2.5 Hz, 1H), 7.60 (dd, J=8.7 Hz, 2H), 7.81 (d, J=8.7 Hz, 1H). $^{13}$C NMR (100 MHz, CDCl$_3$) δ ppm: 23.9, 33.4, 55.3, 71.8, 80.0, 105.3, 113.8 (2C), 121.4, 128.9, 130.4 (2C), 131.9, 136.1, 142.9, 147.2, 148.1, 154.4, 160.0. MS (ESI) m/z: 304.3 ([M+H]$^+$, 100). High-resolution mass (ESI): m/z calculated for [M+H]$^+$ $C_{19}H_{18}N_3O$: 304.1450; m/z measured: 304.1458. Purity (HPLC/UV λ at 260 nm): 100%.

Step 2:
To a solution of compound IIIbl (50 mg, 0.166 mmol, 1 equiv.) in DMSO (5 mL) is added CuCl (26 mg, 0.183 mmol, 1.1 equiv). After 8 h at 120° C., the reaction mixture is cooled to room temperature, then 28% $NH_3$ (5 mL) is added, followed by $CH_2Cl_2$ (10 mL) and $H_2O$ (10 mL). The aqueous phase is extracted 3 times with $CH_2Cl_2$, then the combined organic phases are washed twice with saturated aqueous NaCl solution, dried over MgSO$_4$, then concentrated. After purification on silica (85:15/DCM:AcOEt), product Ibl is obtained (30.2 mg, 62%). $^1$H NMR (400 MHz, CDCl$_3$) δ ppm: 2.87 (s, 3H), 3.90 (s, 3H), 7.07 (d, J=8.8 Hz, 2H), 7.59 (dd, J=8.0, 4.1 Hz, 1H), 7.75 (d, J=8.8 Hz, 2H), 8.12 (d, J=9.3 Hz, 1H), 8.23 (d, J=9.3 Hz, 1H), 9.03 (brs, 1H), 9.45 (dd, J=8.0 and 0.8 Hz, 1H). $^{13}$C NMR (100 MHz, CDCl$_3$) δ ppm: 24.4, 55.4, 113.9 (2C), 122.0 (br), 126.4 (br), 129.8, 130.8 (2C), 131.2, 132.1, 132.5, 138.2, 139.7, 148.9 (br), 151.2 (br), 152.4, 152.8, 160.4. MS (ESI) m/z: 302.2 ([M+H]$^+$, 100). High-resolution mass (ESI): m/z calculated for [M+H]$^+$ $C_{19}H_{16}N_3O$: 302.1293; m/z measured: 302.1296. Purity (HPLC/UV λ at 260 nm): 100%.

The following compounds were also synthesized according to this procedure:

Iaa:
$^1$H NMR (300 MHz, CDCl$_3$) δ 9.47 (ddd, J=8.3, 1.8, 0.5 Hz, 1H), 9.09 (dd, J=4.4, 1.8 Hz, 1H), 8.96 (d, J=2.0 Hz, 1H), 8.94 (d, J=2.0 Hz, 1H), 8.30 (dd, J=9.3, 0.5 Hz, 1H), 8.20 (d, J=9.3 Hz, 1H), 7.68 (dd, J=8.3, 4.4 Hz, 1H).

Ibn:
Yield: 61% (30.5 mg). $^1$H NMR (300 MHz, CDCl$_3$) δ 9.47 (d, J=7.9 Hz, 1H), 9.04 (d, J=4.4 Hz, 1H), 8.25 (d, J=9.3 Hz, 1H), 8.15 (d, J=9.3 Hz, 1H), 7.68 (d, J=7.2 Hz, 2H), 7.60 (dd, J=8.3, 4.4 Hz, 1H), 7.36 (d, J=7.6 Hz, 2H), 2.87 (s, 3H), 2.47 (s, 3H). $^{13}$C NMR (75 MHz, CDCl$_3$) δ 153.31, 152.55, 151.32, 148.88, 139.88, 139.13, 138.21, 136.06, 132.55, 132.24, 129.84, 129.28 (2C), 129.14 (2C), 126.41, 121.98, 24.23, 21.35. MS (ESI) m/z: 286.2 ([M+H]+, 100). High-resolution mass (ESI): m/z calculated for [M+H]$^+$ $C_{19}H_{16}N_3$: 286.1344; m/z measured: 286.1344. Purity (HPLC/UV) at 260 nm): 100%.

Ibf:
Yield: 51% (25.2 mg). $^1$H NMR (300 MHz, CDCl$_3$) δ 9.41 (d, J=8.3 Hz, 1H), 9.00 (brs, 1H), 8.20 (d, J=9.2 Hz, 1H), 8.10 (d, J=9.2 Hz, 1H), 7.52 (dd, J=7.9, 3.8 Hz, 1H), 6.91 (s, 2H), 3.89 (s, 9H), 2.82 (s, 3H). $^{13}$C NMR (75 MHz, CDCl$_3$) δ 153.23, 153.11, 152.47, 151.42 (br), 148.90 (br), 140.06, 138.87, 138.02, 134.27, 132.54 (2C), 129.80, 126.29 (br), 122.06, 106.67 (2C), 60.96, 56.31 (2C), 24.27. MS (ESI) m/z: 362.2 ([M+H]+, 100). High-resolution mass (ESI): m/z calculated for [M+H]$^+$ $C_{21}H_{20}N_3O_3$: 362.1505; m/z measured: 362.1503. Purity (HPLC/UV λ at 260 nm): 100%.

Ibo:
Yield: 64% (30.4 mg). $^1$H NMR (300 MHz, CDCl$_3$) δ 9.47 (d, J=8.2 Hz, 1H), 9.09 (s, 1H), 8.29 (d, J=8.8 Hz, 1H), 8.18 (d, J=7.8 Hz, 1H), 7.75 (d, J=8.5 Hz, 2H), 7.66 (brs, 1H), 7.55 (d, J=8.5 Hz, 2H), 2.87 (s, 3H). $^{13}$C NMR (100 MHz, CDCl$_3$) δ 152.29, 152.05, 151.78-149.58 (br), 149.59-148.60 (br), 140.28, 138.33, 137.35, 135.39, 132.85, 132.48, 130.76 (2C), 128.75 (2C), 123.16-121.57 (br), 24.15. MS (ESI) m/z: 306.1, ([M+H]$^+$, 100), 308.1 ([M+H]$^+$, 40). High-resolution mass (ESI): m/z calculated for [M+H]$^+$ $C_{18}H_{13}C_1N_3$: 306.0798; m/z measured: 306.0800. Purity (HPLC/UV λ at 260 nm): 100%.

Ibp:
Yield: 50% (196.0 mg). $^1$H NMR (400 MHz, CDCl$_3$) δ 9.46 (dd, J=8.2, 1.2 Hz, 1H), 9.08 (s, 1H), 8.30 (d, J=9.3 Hz, 1H), 8.17 (d, J=9.3 Hz, 1H), 7.91 (d, J=1.2 Hz, 1H), 7.68-7.60 (m, 3H), 2.88 (s, 3H). $^{13}$C NMR (101 MHz, CDCl$_3$) δ 152.09, 151.69, 150.71, 149.01, 140.53, 138.80, 133.60, 133.16, 132.94, 132.53, 131.44, 130.45, 129.78, 128.56, 126.29, 122.30, 24.09. MS (ESI) m/z: 242.1 ([M+H]$^+$, 100) and 344.1 ([M+H]$^+$, 50). High-resolution mass (ESI): m/z calculated for [M+H]$^+$ $C_{18}H_{12}C_{12}N_3$: 340.0408; m/z measured: 340.0405. Purity (HPLC/UV k at 264 nm): 94%.

Ibh:
Yield: 52% (19.0 mg). $^1$H NMR (300 MHz, CDCl$_3$) δ 9.46 (d, J=8.3 Hz, 1H), 9.06 (s, 1H), 8.27 (d, J=9.3 Hz, 1H), 8.16 (d, J=9.3 Hz, 1H), 7.78 (ddd, J=8.7, 5.3 Hz, 2H), 7.63 (dd, J=8.1, 4.2 Hz, 1H), 7.26 (t, J=8.6 Hz, 2H), 2.87 (s, 3H). $^{13}$C NMR (75 MHz, CDCl$_3$) δ 163.28 (d, J=249.5 Hz), 152.32, 152.18, 151.49, 148.91, 140.10, 138.20, 134.93 (d, J=3.3 Hz, 2C), 132.60, 132.50, 131.32 (d, J=8.2 Hz, 2C), 129.80, 126.31, 122.11, 115.55 (d, J=21.7 Hz), 24.21. MS (ESI) m/z: 290.2 ([M+H]$^+$, 100). High-resolution mass (ESI): m/z calculated for [M+H]$^+$ $C_{18}H_{13}N_3F$: 290.1094; m/z measured: 290.1094. Purity (HPLC/UV λ at 260 nm): 100%.

Ibq:

Yield: 63% (34.5 mg). $^1$H NMR (400 MHz, CDCl$_3$) δ 9.52 (dd, J=8.2, 1.6 Hz, 1H), 9.07 (dd, J=4.4, 1.6 Hz, 1H), 8.29 (d, J=9.3 Hz, 1H), 8.19 (d, J=9.3 Hz, 1H), 7.89 (d, J=8.5 Hz), 7.80 (d, J=8.5, 2H), 7.70 (dd, J=8.5, 1.2 Hz, 2H), 7.64 (dd, J=8.2, 4.4 Hz, 1H), 7.50 (t, J=7.5 Hz, 2H), 7.41 (tt, J=7.5, 1.2 Hz, 1H), 2.94 (s, 3H). $^{13}$C NMR (101 MHz, CDCl$_3$) δ 152.93, 152.57, 151.46, 148.97, 142.01, 140.40, 140.11, 138.33, 137.79, 132.60, 132.53, 129.88 (3C), 128.92 (2C), 127.75, 127.20 (4C), 126.45, 122.09, 77.00, 24.30. MS (ESI) m/z: 348.2 ([M+H]$^+$, 100). High-resolution mass (ESI): m/z calculated for [M+H]$^+$ C$_{24}$H$_{17}$N$_3$: 340.0408; m/z measured: 340.0405. Purity (HPLC/UV λ at 260 nm): 100%.

Ibj:

Yield: 61% (30.1 mg). $^1$H NMR (400 MHz, CDCl$_3$) δ 9.57 (d, J=6.7 Hz, 1H), 9.42-8.68 (brs, 1H), 8.35 (brs, 1H), 8.25 (s, 1H), 8.24 (brs, 1H), 8.04 (d, J=8.4 Hz, 1H), 7.98 (dd, J=6.4 and 5.0 Hz, 1H), 7.96 (dd, J=6.4 and 5.0 Hz, 1H), 7.91 (dd, J=8.5, 1.6 Hz, 1H), 7.74 (m, 1H), 7.63-7.55 (m, 2H), 2.95 (s, 3H). $^{13}$C NMR (101 MHz, CDCl$_3$) δ 153.35, 152.81, 140.17, 136.34, 133.40, 133.04, 129.82, 129.08, 128.50, 128.24, 127.81, 127.02, 126.72, 126.66, 24.32. MS (ESI) m/z: 322.2 ([M+H]$^+$, 100). High-resolution mass (ESI): m/z calculated for [M+H]$^+$ C$_{24}$H$_{18}$N$_3$: 348.1501; m/z measured: 348.1499. Purity (HPLC/UV λ at 260 nm): 100%.

Example 2: Synthesis of Compound Iad

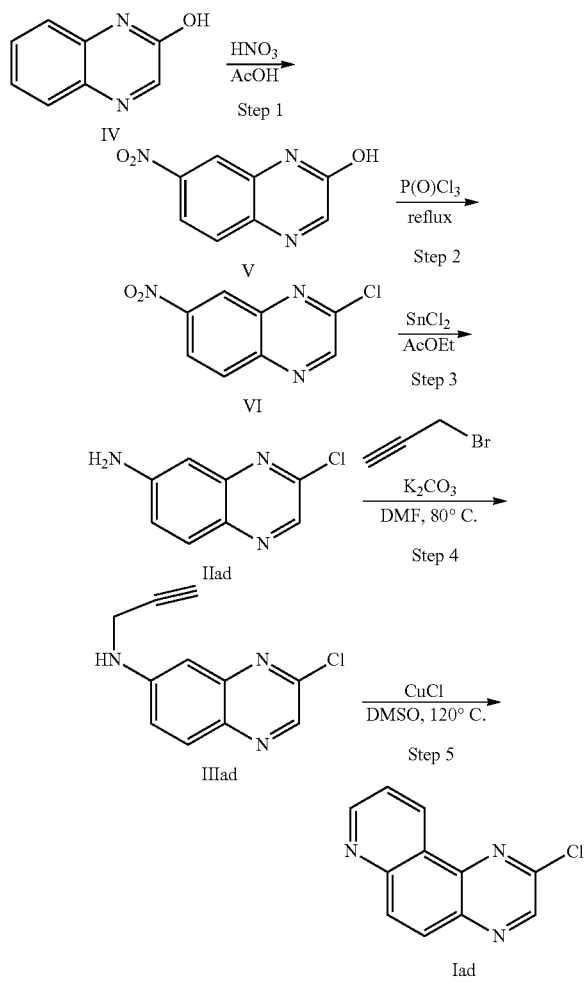

Step 1:

To a solution of commercial 2-quinoxalinol (20.0 g, 0.137 mol, 1 equiv.) in acetic acid (200 mL) placed at 0° C., a 70% nitric acid solution (17.4 mL, 0.274 mol, 2 equiv.) diluted in 20 mL acetic acid is added dropwise. The reaction mixture is then allowed to return to room temperature. After 3 h at room temperature, the colour of the reaction mixture turns from brown to orange-yellow. The precipitate is collected by filtration and washed with water. The orange-yellow solid obtained is dried under vacuum for 48 h to give 17.57 g of compound V (67%). $^1$H NMR (300 MHz, Acetone-d$_6$) δ ppm 9.14 (s, 2H), 8.93 (d, J=2.5 Hz, 1H), 8.61 (dd, J=9.1, 2.5 Hz, 1H), 8.35 (d, J=9.1 Hz, 1H).

Step 2:

To a solution of compound V (17.570 g, 91.50 mmol, 1 equiv.) in 80 mL of POCl$_3$ are added 30 drops of dimethylformamide. The reaction mixture is then refluxed for 3 h. The colour of the reaction mixture turns black. After cooling, the reaction mixture is poured slowly into a 500-mL beaker filled with crushed ice. The precipitate is collected by filtration and washed with water. The solid obtained is dried under vacuum for 48 h to give compound VI in the form of a grey solid (17.02 g, 88%). $^1$H NMR (300 MHz, CDCl$_3$) δ ppm: 8.30 (d, J=9.3 Hz, 1H), 8.56 (dd, J=9.3 and 2.2 Hz, 1H), 8.92 (d, J=2.5 Hz, 1H), 8.93 (s, 1H). $^{13}$C NMR (75 MHz, CDCl$_3$) δ ppm: 123.7, 124.8, 131.1, 141.1, 143.2, 148.0, 148.7, 149.8.

Step 3:

To a suspension of nitro compound VI (14.36 g, 68.5 mmol, 1 equiv.) in AcOEt (300 mL) is added SnCl$_2$.2H$_2$O (45.5 g, 239.9 mmol, 3.5 equiv.), then the reaction mixture is refluxed for 2 h. After cooling, 50% NaOH (6 equiv., 480 mmol) is added slowly at 0° C. and the reaction mixture is filtered on a silica gel pad and then eluted with hot acetone. After concentration, the residue is purified by recrystallisation with CHCl$_3$/petroleum ether to afford compound IIad in the form of a yellow solid (9.65 g, 78%). $^1$H NMR (300 MHz, CDCl$_3$) δ ppm: 4.30 (brs, 2H), 7.03 (d, J=1.7 Hz, 1H), 7.15 (dd, J=8.8, 1.7 Hz, 1H), 7.85 (d, J=8.8 Hz, 1H), 8.47 (s, 1H). $^{13}$C NMR (75 MHz, CDCl$_3$) δ ppm: 107.2, 121.7, 130.3, 135.98, 140.3, 144.2, 147.7, 149.1. High-resolution mass (ESI): m/z calculated for [M+H]$^+$ C$_8$H$_7$N$_3$Cl: 180.0329; m/z measured: 180.0326.

Step 4:

Compound IIIad was prepared from compound IIad according to the procedure described in Example 1.

Step 5:

Compound Iad was prepared from compound IIiad according to the procedure described in Example 1. $^1$H NMR (300 MHz, CDCl$_3$) δ 9.40 (ddd, J=8.3, 1.7, 0.6 Hz, 1H), 9.12 (dd, J=4.4, 1.7 Hz, 1H), 8.91 (s, 1H), 8.31 (dd, J=9.3, 0.6 Hz, 1H), 8.20 (d, J=9.3 Hz, 1H), 7.69 (dd, J=8.3, 4.4 Hz, 1H). $^{13}$C NMR (75 MHz, CDCl$_3$) δ 152.52, 149.36, 147.42, 144.95, 140.28, 140.13, 133.10, 132.92, 129.73, 125.43, 122.53. IR: 3049, 1493, 1207, 1146, 900, 841.

Example 3: Synthesis of Compound Iaj

A suspension of chloro compound Iad (100 mg, 0.464 mmol, 1 equiv.), K$_2$CO$_3$ (16.8 mg, 1.186 mmol, 2.6 equiv.), 2-naphthyl-boronic acid (102 mg, 0.593 mmol, 1.3 equiv.) and PdCl$_2$(PPh$_3$)$_2$ (10 mg, 0.0139 mmol, 0.03 equiv.) in a dioxane/H$_2$O mixture (4 mL/1 mL) is heated to reflux for 1 h. After cooling, the reaction mixture is extracted three times with ethyl acetate and washed once with 10% K$_2$CO$_3$ solution. After drying over MgSO$_4$, filtration and concentration, the residue is purified on silica column (eluent CH₂Cl₂:AcOEt, 77:33) to give compound Iaj in the form of a pale yellow solid (121 mg, 85%). $^1$H NMR (300 MHz, CDCl₃) δ ppm: 7.58 (dd, J=3.5, 6.6 Hz, 1H), 7.60 (dd, J=3.5, 6.6 Hz, 1H), 7.73 (dd, J=8.2, 4.3 Hz, 1H), 7.94 (m, 1H), 8.05 (t, J=4.3 Hz, 1H), 8.07 (d, J=8.2 Hz, 1H), 8.26 (d, J=9.4 Hz, 1H), 8.30 (d, J=9.4 Hz, 1H), 8.50 (dd, J=9.6, 1.6 Hz, 1H), 8.76 (brs, 1H), 9.13 (dd, J=4.5, 1.6 Hz, 1H), 9.60 (s, 1H), 9.70 (dd, J=8.2, 1.7 Hz, 1H). $^{13}$C NMR (75 MHz, CDCl₃) δ ppm: 122.2, 124.4, 126.6, 126.8, 127.4, 127.8, 128.9, 129.1, 130.3, 132.9, 133.4, 133.9, 134.2, 140.0, 140.7, 143.1, 149.5, 150.7, 151.97, 152.0. IR: 1728, 1701, 1539, 1499, 1380, 1287, 1237, 1210, 1090, 1016, 845, 825, 791, 751, 732. High-resolution mass (ESI): m/z calculated for [M+H]⁺ C₂₁H₁₄N₃: 308.1188; m/z measured: 308.1188.

The following compounds were also synthesized according to this procedure:

Iac:
$^1$H NMR (400 MHz, CDCl₃) δ 9.66 (d, J=8.3 Hz, 1H), 9.46 (s, 1H), 9.15 (brs, 1H), 8.33 (dd, J=8.3 and 1.5 Hz, 2H), 8.26 (t, J=8.5 Hz, 2H), 7.72 (brm, 1H), 7.61 (m, 3H). $^{13}$C NMR (100 MHz, CDCl₃) δ 122.3 (br), 126.8 (br), 127.5 (2C), 129.2 (2C), 130.2, 130.3, 132.4, 132.8, 136.5, 140.1, 140.7, 142.9, 149.7 (br), 150.7, 151.9 (br). High-resolution mass (ESI): m/z calculated for [M+H]⁺ C₁₇H₁₂N₃: 258.1031; m/z measured: 258.1028.

Iae:
$^1$H NMR (300 MHz, DMSO) δ 9.80 (brs, 1H, OH), 9.65 (s, 1H), 9.56 (dd, J=8.3, 1.7 Hz, 1H), 9.14 (dd, J=4.3, 1.7 Hz, 1H), 8.26 (s, 2H), 7.93-7.87 (m, 2H), 7.88 (dd, J=8.4, 4.4 Hz, 1H), 7.44 (t, J=8.2 Hz, 1H), 7.01 (ddd, J=8.2, 2, 1 Hz 1H). $^{13}$C NMR (75 MHz, DMSO) δ 158.14, 152.20, 150.10, 148.75, 143.50, 140.15, 138.90, 137.17, 132.07, 131.99, 130.26, 130.03, 125.76, 122.78, 118.26, 117.67, 114.04, 39.52. High-resolution mass (ESI): m/z calculated for [M+H]⁺ C₁₇H₁₂N₃O: 274.0980; m/z measured: 274.0978.

Iaf:
$^1$H NMR (300 MHz, CDCl₃) δ 9.59 (ddd, J=8.3, 1.7, 0.5 Hz, 1H), 9.39 (s, 1H), 9.12 (dd, J=4.4, 1.7 Hz, 1H), 8.29 (dd, J=9.4, 0.5 Hz, 1H), 8.23 (d, J=9.4 Hz, 1H), 7.71 (dd, J=8.3, 4.4 Hz, 1H), 7.55 (s, 2H), 4.06 (s, 6H), 3.97 (s, 2H). $^{13}$C NMR (75 MHz, CDCl₃) δ 154.11, 152.12, 150.63, 149.67, 142.97, 140.79, 140.66, 139.96, 132.91, 132.47, 132.16, 130.44, 126.63, 122.31, 105.11, 61.22, 56.62. IR 3000-2837, 1588, 1494, 1343, 1235, 1127, 853. High-resolution mass (ESI): m/z calculated for [M+H]⁺ C₂₀H₁₈N₃: 348.1348; m/z measured: 348.1353.

Iah:
$^1$H NMR (300 MHz, CDCl₃) δ 9.58 (ddd, J=8.3, 1.7, 0.6 Hz, 1H), 9.38 (s, 1H), 9.10 (dd, J=4.4, 1.7 Hz, 1H), 8.31 (dd, J=9.0, 5.4 Hz, 2H), 8.27 (dd, J=9.3, 0.6 Hz, 2H), 8.20 (d, J=9.3 Hz, 2H), 7.68 (dd, J=8.3, 4.4 Hz, 1H), 7.28 (t, J=8.5 Hz, 2H). $^{13}$C NMR (75 MHz, CDCl₃) δ 164.35 (d, J=251.1 Hz), 152.00, 149.58 (d, J=14.0 Hz), 142.49, 140.64, 139.84, 132.74, 132.48, 130.19, 129.40 (d, J=8.5 Hz), 126.47, 122.18, 116.30 (d, J=21.7 Hz). $^{19}$F NMR (188 MHz, CDCl₃) δ 110.66 (tt, J=8.5, 5.4 Hz). High-resolution mass (ESI): m/z calculated for [M+H]⁺ C₁₇H₁₁N₃F: 276.0937; m/z measured: 276.0937.

Iam:
$^1$H NMR (300 MHz, DMSO) δ 10.01 (d, J=1.9 Hz, 1H), 9.95 (s, 1H), 9.71 (dd, J=8.3, 1.5 Hz, 1H), 9.49 (d, J=2.0 Hz, 1H), 9.17 (dd, J=4.2, 1.5 Hz, 1H), 8.31 (s, 2H), 8.21 (d, J=7.4 Hz, 1H), 8.15 (d, J=8.3 Hz, 1H), 7.94-7.85 (m, 2H), 7.74 (ddd, J=7.9, 6.9, 0.9 Hz, 1H). $^{13}$C NMR (75 MHz, DMSO) δ 152.40, 149.21, 148.80, 148.27, 148.09, 143.86, 140.47, 139.10, 135.05, 132.57 (2C), 130.97, 130.05, 129.08, 128.88, 128.67, 127.49, 127.33, 125.76, 122.94, 39.52. IR: 3048, 1572, 1498, 1300, 1090, 1066, 904, 847, 790, 753. High-resolution mass (ESI): m/z calculated for [M+H]⁺ C₂₀H₁₃N₄: 309.1140; m/z measured: 309.1140.

Iai:
$^1$H NMR (300 MHz, CDCl₃) δ 9.57 (ddd, J=8.3, 1.7, 0.6 Hz, 1H), 9.29 (s, 1H), 9.12 (dd, J=4.4, 1.8 Hz, 1H), 8.37 (dd, J=9.3, 0.5 Hz, 1H), 8.34 (m, 1H), 8.31 (dd, J=9.3 Hz, 1H), 8.05 (brd, J=8.2 Hz, 1H), 8.00 (dd, J=6.9, 2.5 Hz, 1H), 7.86 (dd, J=7.1, 1.2 Hz, 1H), 7.72-7.63 (m, 2H), 7.63-7.51 (m, 2H). $^{13}$C NMR (75 MHz, CDCl₃) δ 153.32, 152.00, 149.43, 146.47, 140.46, 139.92, 134.98, 134.12, 132.97, 132.79, 131.21, 130.32, 130.27, 128.86, 128.69, 127.17, 126.61, 126.36, 125.41, 125.13, 122.32. IR 3000-2800, 1755, 1586, 1574, 1495, 1377, 1317, 1303, 1088, 1055, 899, 844, 795, 775, 732. High-resolution mass (ESI): m/z calculated for [M+H]⁺ C₂₁H₁₄N₃: 308.1188; m/z measured: 308.1187.

Ia:
$^1$H NMR (300 MHz, CDCl₃) δ 9.61 (ddd, J=8.3, 1.7, 0.6 Hz, 1H), 9.55 (d, J=1.7 Hz, 1H), 9.46 (s, 1H), 9.13 (dd, J=4.4, 1.8 Hz, 1H), 8.80 (dd, J=4.7, 1.2 Hz, 1H), 8.61 (ddd, J=8.0, 2.2, 1.7 Hz, 1H), 8.32 (dd, J=9.3, 0.5 Hz, 1H), 8.25 (d, J=9.3 Hz, 1H), 7.72 (dd, J=8.3, 4.4 Hz, 1H), 7.54 (ddd, J=8.0, 4.9, 0.7 Hz, 1H). $^{13}$C NMR (75 MHz, CDCl₃) δ 152.21, 151.12, 149.52, 148.76, 148.38, 142.45, 141.28, 140.12, 134.67, 133.17, 132.78, 132.26, 130.18, 126.43, 123.90, 122.40. IR: 3040, 1614, 1589, 1496, 1477, 1391, 1304, 1289, 1095, 1075, 845, 790, 702. High-resolution mass (ESI): m/z calculated for [M+H]⁺ C₁₆H₁₁N₄: 259.0984; m/z measured: 259.0984.

Example 4: Synthesis of Compound Iak

To a solution of chloro compound Iad (100 mg, 0.464 mmol, 1 equiv.) in 5 mL THF is added trimethylsilylacetylene (260 μL, 1.85 mmol, 4 equiv.), CuI (4.3 mg, 0.0232 mmol, 0.05 equiv.), PdCl₂(PPh₃)₂ (6.5 mg, 0.0093 mmol, 0.02 equiv) and then triethylamine (3 mL). The reaction mixture is heated to reflux under argon atmosphere for 48 h, then cooled to room temperature. The reaction mixture is filtered on a silica pad, and eluted with ethyl acetate. After concentration, the residue is taken up in methanol (10 mL), potassium carbonate is added (500 mg) and the reaction mixture is heated for 10 min at reflux. After cooling, the reaction mixture is diluted with water (20 mL), extracted with AcOEt three times (30 mL) and washed with brine twice (30 mL). After drying over MgSO₄ and filtration, the reaction mixture is purified on silica gel to give a brown solid corresponding to compound Iak (48 mg, 50%). $^1$H NMR (300 MHz, CDCl₃) δ ppm: 3.50 (s, 1H), 7.70 (dd, J=8.3, 4.3 Hz, 1H), 8.20 (d, J=9.4 Hz, 1H), 8.32 (d, J=9.4 Hz, 1H), 9.04 (s, 1H), 9.11 (dd, J=4.4, 1.7 Hz, 1H), 9.50 (dd, J=8.2, 1.7 Hz, 1H). $^{13}$C NMR (75 MHz, CDCl₃) δ ppm: 81.0, 81.6, 122.6, 125.9, 130.1, 133.0, 133.9, 137.4, 140.2, 140.8, 147.7, 149.3, 152.3.

Example 5: Synthesis of Compound Xbc

Step 1:
To a solution of compound IIbc (500.0 mg, 2.13 mmol, 1 equiv.) in a THF/water mixture (10.5/1 mL) in the presence of 10 mg of CuCl₂ (catalytic amount) and 10 mg of copper (catalytic amount) under inert nitrogen atmosphere are added 0.41 mL of triethylamine (2.98 mmol, 1.4 equiv.) and 0.34 mL of 3-chloro-3-methyl-1-butyne (2.98 mmol, 1.4 equiv.). The reaction mixture is stirred at room temperature for 12 h, hydrolysed by 15 mL of saturated K₂CO₃ solution, then extracted 3 times with DCM. The organic phases are combined, washed with saturated NaCl solution, dried over $Na_2SO_4$ then concentrated under reduced pressure. Purification by chromatography on silica gel in a DCM:ethyl acetate mixture in 85:15 proportions made it possible to obtain the corresponding N-alkyl compound (9bc). Yield: 65% (414.0 mg). $^1$H NMR (400 MHz, $CDCl_3$) δ ppm: 1.68 (s, 6H), 2.40 (s, 1H), 2.66 (s, 3H), 4.32 (brs, 1H, NH), 7.16 (dd, J=9.0, 2.5 Hz, 1H), 7.41-7.50 (m, 3H), 7.56 (d, J=2.5 Hz, 1H), 7.61 (d, J=8.3 Hz, 2H), 7.81 (d, J=9.0 Hz, 1H). $^{13}$C NMR (100 MHz, $CDCl_3$) δ ppm: 23.6, 30.0 (2C), 47.8, 71.2, 86.4, 108.0, 123.2, 128.4 (2C), 128.5, 128.6, 128.8 (2C), 136.1, 139.6, 142.6, 145.8, 147.8, 154.6. MS (ESI) m/z: 302.3 ($[M+H]^+$, 100). High-resolution mass (ESI): m/z calculated for $[M+H]^+$ $C_{20}H_{20}N_3$: 302.1657; m/z measured: 302.1656. Purity (HPLC/UV λ at 254 nm): 95%.

Step 2:

A solution of compound 9bc (300.0 mg, 1.00 mmol, 1 equiv.) in the presence of 10 mg of CuCl in toluene (5 mL) is refluxed under inert nitrogen atmosphere for 1 h. After cooling, the reaction mixture is hydrolysed by 10 mL of saturated $K_2CO_3$ solution then extracted with DCM. The combined organic phases are washed with saturated NaCl solution, dried over $Na_2SO_4$, then evaporated under reduced pressure. Purification by chromatography on silica gel in a DCM:AcOEt mixture in 10:0 to 8:2 proportions made it possible to obtain compound Xbc. Yield: 64% (191.0 mg). $^1$H NMR (400 MHz, $CDCl_3$) δ ppm: 1.38 (s, 6H), 2.69 (s, 3H), 4.07 (brs, NH, 1H), 5.52 (d, J=9.8 Hz, 1H), 6.93 (d, J=8.8 Hz, 1H), 7.42 (d, J=9.8 Hz, 1H), 7.45-7.52 (m, 3H), 7.65 (d, J=8.8 Hz, 1H), 7.70 (dd, J=8.0, 1.5 Hz, 2H). $^{13}$C NMR (100 MHz, $CDCl_3$) δ ppm: 23.8, 31.4 (2C), 52.6, 111.7, 118.8, 119.9, 128.0, 128.2 (2C), 128.6, 128.7, 129.2 (2C), 135.7, 138.3, 139.9, 143.0, 147.0, 153.7. MS (ESI) m/z: 302.3 ($[M+H]^+$, 100).

II. Biological Evaluation

The compounds of the invention were evaluated for their neuroprotective and neural differentiation (or neuritogenic) properties.

II.1 Effect of the Compounds on Neuroprotection and Differentiation of Dopaminergic Neurons Derived from Primary Cultures of Embryonic Ventral Mesencephalon.

The compounds of the invention were tested in a model of spontaneous degeneration of dopaminergic neurons derived from primary cultures of embryonic ventral mesencephalon according to the protocol described in the article by S. Guerreiro et al. (2008). The primary cultures of embryonic ventral mesencephalon thus obtained are mixed cultures containing about 50% neuronal cells and 50% glial cells. Among the neuronal cells, dopaminergic neurons make up 3% of the total neurons, most of the neurons derived from these cultures being GABAergic. Concerning the glial cells, they mainly consist of astrocytes (>95% of the glial cells). These cultures are characterized by spontaneous, progressive and selective death of dopaminergic neurons as a result of a mechanism involving immature astrocytes and calcium dyshomeostasis (E. Rousseau et al. (2013), D. Toulorge et al. (2011)). The neuroprotective effect of the compounds of the invention was evaluated by counting dopaminergic ($TH^+$) neurons stained by tyrosine hydroxylase (TH) immunohistochemistry after 10 days of culture (DIV 10). The observation at DIV 10 is directly related to the fact that, according to the literature, a large decrease in the number of $TH^+$ neurons is observed after 10 days of culture in the absence of neuroprotective treatment.

The results obtained are presented in Table 1 below.

TABLE 1

Neuroprotective activity of the compounds of the invention on survival of dopaminergic neurons derived from embryonic ventral mesencephalon.

| | % relative to the control ± standard error | | |
|---|---|---|---|
| Compounds | $TH^{+a}$ neurons 100 nM | $TH^{+a}$ neurons 1 μM | $TH^{+a}$ neurons 10 μM |
| Control | | 26.0 ± 0.5 | |
| db-cAMP[b] | | 100.0 ± 1.4 | |
| Iac | 46.6 ± 2.8 | 64.7 ± 2.9* | 91.0 ± 3.7* |
| Iaa | 25.7 ± 1.6 | 26.2 ± 1.7 | 30.6 ± 2.3 |
| Iad | 27.4 ± 1.6 | 26.5 ± 1.6 | 33.8 ± 1.8 |
| Iae | 24.7 ± 1.6 | 47.7 ± 2.6* | 99.3 ± 4.4* |
| Iaf | 27.7 ± 1.6 | 46.8 ± 2.3* | 70.8 ± 3.5* |
| Iag | 31.4 ± 1.7 | 48.3 ± 2.4* | 96.6 ± 4.5* |
| Iam | 27.6 ± 2.0 | 46.7 ± 2.7* | 97.3 ± 3.6* |
| Iah | 24.4 ± 1.4 | 32.8 ± 1.8 | 42.8 ± 2.2* |
| Iaj | 28.9 ± 1.8 | 42.8 ± 2.1* | 94.9 ± 3.5* |
| Iak | 38.2 ± 2.1* | 40.7 ± 2.6* | 7.0 ± 1.3* |
| Ibj | 58.1 ± 2.8 | 59.2 ± 2.2 | 67.3 ± 2.5* |

[a]Number of $TH^+$ neurons per well expressed as a percentage relative to cultures treated with 1 mM db-cAMP. The standard error of the mean is obtained on three independent experiments for the active compounds, the conditions of which are replicated three times.
[b]db-cAMP used at a concentration of 1 nM.
Statistical analyses: *p < 0.05, vs control, one-way ANOVA followed by a Dunnett's post-hoc analysis.

The results show a particularly high activity of compounds Iac, Iae, Iag, Iaj and Iam with a survival percentage at 10 μM almost equal to that induced by db-cAMP at 1 mM.

II.2 Study of Blood-Brain Barrier Crossing of Compound Iac

Compound Iac is a 3-phenyl-1,4,8-triazaphenanthrene. In vitro, it has neuroprotective activity at a concentration of 1 μM for an optimal activity at 10 μM.

The physicochemical properties of compound Iac were compared with the theoretical physicochemical properties expected for a centrally-active compound and then blood-brain barrier crossing was evaluated.

II.2.1 Prediction of the ability of a molecule to passively cross the BBB of the CNS (QSARs)[a]

A comparison between the physicochemical properties of Iac and those of the active compounds on the CNS is presented in Table 2 below.

TABLE 2

Comparison between the physicochemical properties of Iac and those of the active compounds on the CNS.

| Physicochemical properties | CNS drugs[a] | Compound Iac |
|---|---|---|
| Activity | < nM | 1 μM |
| Selectivity | High | Unknown |
| Molecular weight | <450 g · mol$^{-1}$ | 257 g · mol$^{-1}$ |
| LogP | <5 | 2.4[b] |
| H-bond donor | <3 | 0 |
| H-bond acceptor | <7 | 3 |
| Rotatable bonds | <8 | 1 |
| pKa | 7.5-10.5 (avoid acids) | undetermined |
| Polar surface area (PSA) | <60-70 A° | 39 A°[c] |
| Aqueous solubility | >60 μg · mL$^{-1}$ | <10 μg · mL$^{-1}$ |

[a]See Pajouhesh and Lenz (2005).
[b]The LogP predictions were made with the free online application ALOGPS 2.1, VCCLAB, Virtual Computational Chemistry Laboratory, http://www.vcclab.org, 2005.
[c]Value calculated using molinspiration (www.molinspiration.com)

Compound Iac has, in terms of physicochemical properties, most of the features necessary for its diffusion through the BBB. However, this type of prediction is limited to passive diffusion of the molecule and does not take into account possible interactions with the barrier, such as metabolism by BBB cytochromes, as well as efflux pump or active transport phenomena. An in vivo study of BBB crossing is thus essential to confirm this prediction.

II.2.2 In vivo study of BBB crossing of compound Iac

The goal of this study is to confirm, by HPLC coupled to mass spectrometry, the presence of compound Iac in the brain parenchyma after sub-chronic intravenous treatment in mice.

Animals:

The study is performed with CD-1 mice.

A 0.5 mg/mL solution of compound Iac is prepared in physiological saline containing 10% Cremophor EL®. The same dose of this solution is administered intravenously to 6 mice (2 µL/g).

After 5 min, 3 mice are sacrificed. After 30 min, the other 3 mice are sacrificed.

Blood is drawn, and the plasma is separated by centrifugation. The brain is harvested after intracardiac perfusion. The samples are frozen and stored at −80° C. before treatment.

Sample Treatment:

Plasma: 400 µL of each plasma sample is mixed with 1 mL of acetonitrile to precipitate proteins and extract compound Iac.

Brain: Each brain is ground in 400 µL of physiological saline. 800 µL of acetonitrile is added in order to extract compound Iac.

Extraction:

The treated samples are vortexed for 3 minutes and then placed in a sonicator again for 3 minutes. The precipitated proteins and the solid residues are sedimented by centrifugation (15,000 g, 5 minutes at 4° C.). The supernatants are transferred to a microplate to be analysed by HPLC-MS/MS.

HPLC-MS/MS Analysis:

Samples are analysed with the method described below, with detection and quantification, based on peak area, being performed by HPLC-MS/MS in MRM mode.

Standard solutions are analysed in the same series of injections.

For the calculation of log [brain]/[plasma] to determine blood-brain barrier crossing, the mean plasma volume of a mouse is evaluated at 1.5 mL.

First, FIA is performed as described below in order to choose the proper analytical conditions for MS/MS. It is performed by injecting directly into the mass spectrometer pure product Iac diluted in solvent. There is thus no HPLC separation since it is a control solution and not a brain extract. A solution of compound Iac is flow-injected into the mass spectrometer, and the voltages are adjusted to obtain an optimal intensity for the molecular ion and one or two daughter ions obtained by fragmentation of the molecular ion.

Flow Injection Analysis (FIA):

A 1 mg/mL solution of compound Iac is prepared in acetonitrile. This solution is diluted 1/100.

The development of the analysis is performed with a UHPLC coupled to a triple quadrupole Shimadzu LC-MS 8030. The system is used in FIA mode.

1 µL of the diluted solution is injected.

The molecular ion analysis conditions are optimized (source, ionization). The m/z ratio of the molecular ion is adjusted. The voltages are adjusted (Q1, collision cell, Q3). The one or more best fragments are selected, and their m/z ratios adjusted.

HPLC-MS/MS Method in MRM Mode:

A 10 mM solution of compound Iac in DMSO is diluted to a M-order concentration to develop the analytical method.

The chromatographic conditions are optimized (solvents, pH, elution mode, flow rate, etc.).

The chromatograms are recorded by injecting preferably 1 µL of solution.

Calibration for Plasma Assay:

Standards are prepared from 5 dilutions of compound Iac in mouse plasma. Samples in plasma are treated and extracted as previously indicated.

Collection (Plasma):

The concentration considered is 1 µM (n=2).

The samples are prepared in the same way as for the calibration, but, in this case, the plasma does not contain compound Iac. The latter is present in acetonitrile in sufficient amount to arrive at a concentration equivalent to 1 µM in plasma.

Calibration for Brain Assay:

Standards are prepared from 5 dilutions of compound Iac in mouse brains ground in 400 µL of saline solution. The samples in brains are treated and extracted as previously indicated.

Collection (Brain):

The amount considered is 1 nmol (n=2).

The samples are prepared in the same way as for the calibration, but, in this case, the brain does not contain compound Iac. The latter is present in acetonitrile in sufficient amount to arrive at an amount equivalent to 1 nmol per brain:

Once the calibration and collection steps are performed, the samples taken from the treated animals, then treated and extracted as previously indicated, are analysed.

Result:

The results obtained are presented in the table below.

| Waiting period before euthanasia after IV injection of 1 mg/kg of Iac | Plasma concentration (nmol/mL) | Amount (nmol/brain) | Log [brain]/[plasma] |
|---|---|---|---|
| 5 min | 2.47 ± 0.24 | 5.19 ± 0.25 | 0.15 ± 0.05 |
| 30 min | 0.32 ± 0.05 | 0.50 ± 0.07 | 0.02 ± 0.10 |

Conclusion:

Compound Iac is able to cross the BBB in vivo after intravenous administration. These results confirm the QSAR predictions.

II.3 In Vivo Tests.

The potential neuroprotective effects of Iac were evaluated by measuring striatum dopamine levels and dopamine turnover in the mouse model of Parkinson's disease treated with MPTP (1-methyl-4-phenyl-1,2,3,6-tetrahydropyridine), and by evaluating the number of dopaminergic neurons saved in the substantia nigra. Mice were treated with Iac (50 and 100 mg/kg, p.o., in 1% carboxymethyl cellulose and 0.5% Tween 80) for 11 consecutive days. MPTP (20 mg/kg; intraperitoneal route), or saline solution for the controls, was administered on treatment days 4 to 8. All mice were killed on day 12 following final administration of the treatment, then the striatal tissue was dissected for analysis. The effect of MPTP treatment on striatum dopamine depletion was analysed by high-pressure liquid chromatography (HPLC) in combination with electrochemical detection for measurement of levels of dopamine monoamine (DA), 3,4-dihydroxyphenylacetic acid (DOPAC), and homovanillic acid (HVA).

Iac (50 mg/kg and 100 mg/kg) increased striatum DA levels (64% and 78%, respectively). Striatum HVA levels were also increased (25%), but only at the highest dose of Iac (100 mg/kg). A decrease in the (DOPAC+HVA)/DA) ratio was observed at 50 mg/kg (30%) and 100 mg/kg (28%) doses of Iac. The Iac treatment had no significant effect on DOPAC levels.

At the dose of 2×25 mg/kg/d (par os), the near-total survival of TH$^+$ neurons was observed. Indeed, in the group of mice treated with MPTP/Iac, survival was measured at 93±4% relative to the controls. At a higher dose (2×50 mg/kg/d), Iac is slightly less active since dopaminergic neuron survival is 81±4% relative to the controls.

These data suggest that treatment with Iac makes it possible to neutralize a portion of the dopamine loss and to attenuate the increase in dopamine turnover, and to protect the dopaminergic neurons of the substantia nigra.

REFERENCES

S. Guerreiro, et al. (2008): "Paraxanthine, the primary metabolite of caffeine, provides protection against dopaminergic cell death via stimulation of ryanodine receptor channels" *Mol. Pharmacol.* 2008, 74 (4), 980e989.
Mourlevat et al. (2003): "Prevention of Dopaminergic Neuronal Death by Cyclic AMP in Mixed Neuronal/Glial Mesencephalic Cultures Requires the Repression of Presumptive Astrocytes" *Molecular Pharmacology* 2003, 64:578-586.
Pajouhesh et Lenz (2005): "Medicinal Chemical Properties of Successful Central Nervous System Drugs" *Neuro Rx.* 2005, 2: 541-553.
E. Rousseau, et al. (2013): "The iron-binding protein lactoferrin protects vulnerable dopamine neurons from degeneration by preserving mitochondrial calcium homeostasis" *Mol. Pharmacol.* 2013, 84, 888e898.
D. Toulorge, et al. (2011): "Neuroprotection of midbrain dopamine neurons by nicotine is gated by cytoplasmic Ca2+" *FASEB J.* 2011, 25, 2563e2573.
WO 2010/007179
WO 2012/131080

The invention claimed is:
1. A compound of following formula (I):

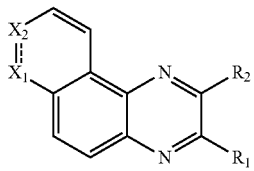

or a pharmaceutically acceptable salt and/or solvate thereof, a stereoisomer, or a mixture of stereoisomers in any proportions,
wherein:
===== is a single or double bond,
$X_1$ is:
$NR_{1a}$ when ===== is a single bond, and
N when ===== is a double bond,
$X_2$ is:
$CR_{2a}R_{2b}$ when ===== is a single bond, and
$CR_{2c}$ when ===== is a double bond,
$R_1$ is a hydrogen or a $(C_1$-$C_6)$alkyl group,
$R_2$ is an aryl or heteroaryl group, optionally substituted by one or more groups selected from a halogen atom, $(C_1$-$C_6)$alkyl, $(C_1$-$C_6)$alkoxy, aryl, $N_3$, $NO_2$, OH, $NH_2$, and —NH—$((C_1$-$C_6)$alkyl), $R_{1a}$ and $R_{2c}$ are each independently a hydrogen atom or a $(C_1$-$C_6)$alkyl group, and
$R_{2a}$ and $R_{2b}$ are each independently a $(C_1$-$C_6)$alkyl group.

2. The compound according to claim 1, being a compound of following formula (Ia):

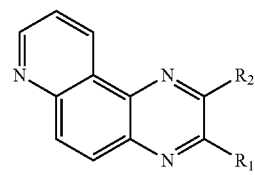

or a pharmaceutically acceptable salt and/or solvate thereof, a stereoisomer, or a mixture of stereoisomers in any proportions,
wherein $R_1$ and $R_2$ are as defined in claim 1.

3. The compound according to claim 1, wherein $R_2$ is an aryl group optionally substituted by one or more groups selected from a halogen atom, $(C_1$-$C_6)$alkyl, $(C_1$-$C_6)$alkoxy, OH and aryl.

4. The compound according to claim 1, wherein $R_2$ is a phenyl, naphthyl, pyridyl, quinoxalyl or quinolyl group, optionally substituted by one or more groups selected from a halogen atom, $(C_1$-$C_6)$alkyl, $(C_1$-$C_6)$alkoxy, aryl, $N_3$, $NO_2$, OH, $NH_2$, and —NH—$((C_1$-$C_6)$alkyl).

5. The compound according to claim 4, wherein $R_2$ is a phenyl group, optionally substituted by one or more groups selected a halogen atom, $(C_1$-$C_6)$alkyl, $(C_1$-$C_6)$alkoxy, OH and aryl.

6. The compound according to claim 4, wherein $R_2$ is a phenyl group, optionally substituted by one or more groups selected $(C_1$-$C_6)$alkoxy and OH.

7. The compound according to claim 1, selected from the following compounds:

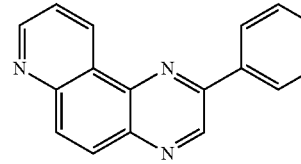

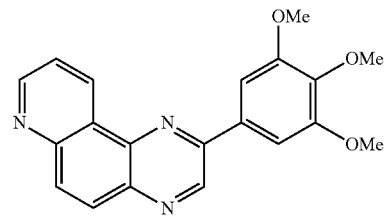

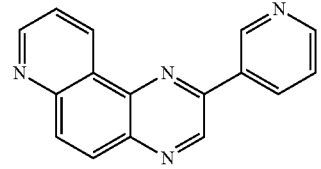

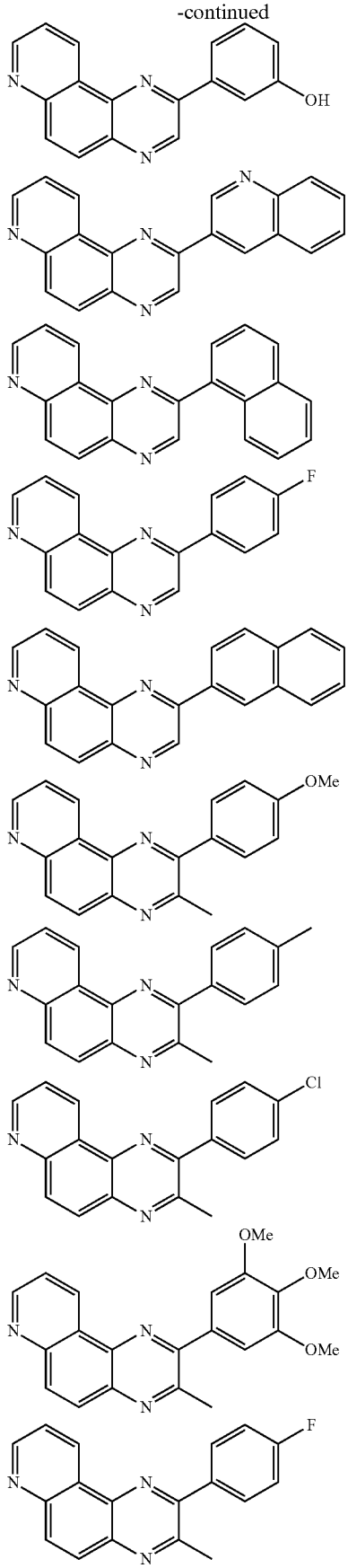

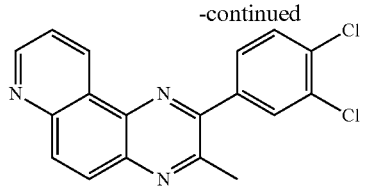

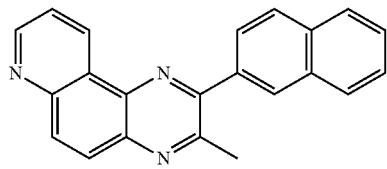

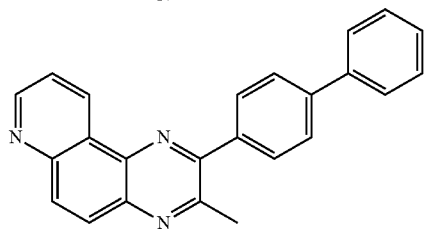

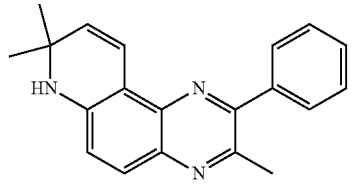

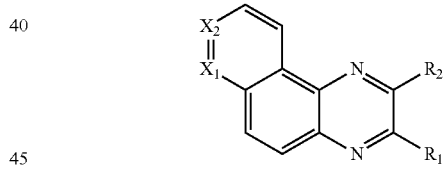

and the pharmaceutically acceptable salts and/or solvates thereof.

8. A method for neurotrophy or neuroprotection comprising administering to a patient in need thereof an effective amount of a compound of following formula (I):

$$\text{(I)}$$

or a pharmaceutically acceptable salt and/or solvate thereof, a stereoisomer, or a mixture of stereoisomers in any proportions, wherein:

===== is a single or double bond, $X_1$ is:
$NR_{1a}$ when ===== is a single bond, and
N when ===== is a double bond, $X_2$ is:
$CR_{2a}R_{2b}$ when ===== is a single bond, and
$CR_{2c}$ when ===== is a double bond, $R_1$ and $R_2$ are each independently a hydrogen atom; a halogen atom; a linear or branched, saturated or unsaturated hydrocarbon chain having from 1 to 10 carbon atoms; an optionally substituted aryl; or an optionally substituted heteroaryl, $R_{1a}$ and $R_{2c}$ are each independently a hydrogen atom or a $(C_1-C_6)$alkyl group, and $R_{2a}$ and $R_{2b}$ are each independently a $(C_1-C_6)$alkyl group.

9. A method for treating a neurodegenerative disease selected from Alzheimer's disease, Parkinson's disease, multiple sclerosis and amyotrophic lateral sclerosis, comprising administering to a patient in need thereof an effective amount of a compound of following formula (I):

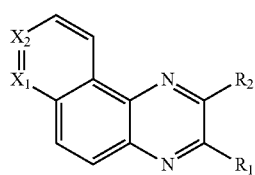

(I)

or a pharmaceutically acceptable salt and/or solvate thereof, a stereoisomer, or a mixture of stereoisomers in any proportions,
wherein:
===== is a single or double bond,
$X_1$ is:
$NR_{1a}$ when ===== is a single bond, and
N when ===== is a double bond,
$X_2$ is:
$CR_{2a}R_{2b}$ when ===== is a single bond, and
$CR_{2c}$ when ===== is a double bond,
$R_1$ and $R_2$ are each independently a hydrogen atom; a halogen atom; a linear or branched, saturated or unsaturated hydrocarbon chain having from 1 to 10 carbon atoms; an optionally substituted aryl; or an optionally substituted heteroaryl,
$R_{1a}$ and $R_{2c}$ are each independently a hydrogen atom or a ($C_1$-$C_6$)alkyl group, and
$R_{2a}$ and $R_{2b}$ are each independently a ($C_1$-$C_6$)alkyl group.

10. The method according to claim 9, wherein the neurodegenerative disease is Parkinson's disease.

11. A pharmaceutical composition comprising at least one compound of formula (I) according to claim 1.

12. A process for preparing a compound of following formula (I):

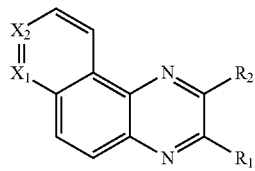

(I)

or a pharmaceutically acceptable salt and/or solvate thereof, a stereoisomer, or a mixture of stereoisomers in any proportions,
wherein:
===== is a single or double bond,
$X_1$ is:
$NR_{1a}$ when ===== is a single bond, and
N when ===== is a double bond,
$X_2$ is:
$CR_{2a}R_{2b}$ when ===== is a single bond, and
$CR_{2c}$ when ===== is a double bond,
$R_1$ and $R_2$ are each independently a hydrogen atom; a halogen atom; a linear or branched, saturated or unsaturated hydrocarbon chain having from 1 to 10 carbon atoms; an optionally substituted aryl; or an optionally substituted heteroaryl,
$R_{1a}$ and $R_{2c}$ are each independently a hydrogen atom or a ($C_1$-$C_6$)alkyl group, and
$R_{2a}$ and $R_{2b}$ are each independently a ($C_1$-$C_6$)alkyl group,
comprising the following successive steps:
(a1) coupling between an amino-quinoxaline of following formula (II):

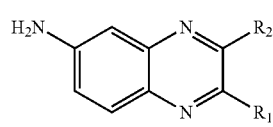

(II)

wherein $R_1$ and $R_2$ are as defined above,
with a propargyl halide of formula CH≡C—$CHR_{2c}$Hal or CH≡C—$CR_{2a}R_{2b}$Hal wherein:
$R_{2a}$ and $R_{2b}$ are each independently a ($C_1$-$C_6$)alkyl group,
$R_{2c}$ is a hydrogen atom or a ($C_1$-$C_6$)alkyl group, and
Hal is a halogen atom,
to give a compound of following formula (IIIa) or (IIIb):

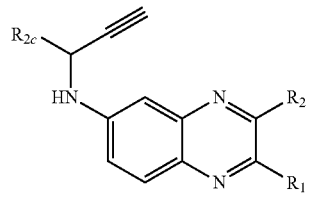

(IIIa)

or

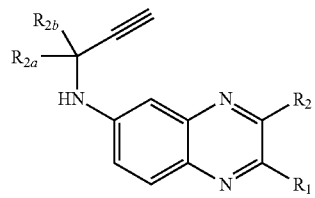

(IIIb)

wherein $R_1$, $R_2$, $R_{2a}$, $R_{2b}$ and $R_{2c}$ are as defined above,
(b1) cycloisomerization of the compound of formula (IIIa) or (IIIb) obtained in the preceding step and aromatization when ===== is a double bond to give a compound of formula (I), and
(c1) optionally salification and/or solvation of the compound of formula (I) obtained in the preceding step to give a pharmaceutically acceptable salt and/or solvate of the compound of formula (I).

13. The process according to claim 12, wherein Hal is Cl, Br or I.

14. A process for preparing a compound of following formula (I):

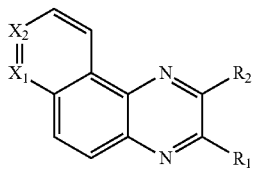

(I)

or a pharmaceutically acceptable salt and/or solvate thereof, a stereoisomer, or a mixture of stereoisomers in any proportions, wherein:

----- is a single or double bond, $X_1$ is:

$NR_{1a}$ when ----- is a single bond, and

N when ----- is a double bond, $X_2$ is:

$CR_{2a}R_{2b}$ when ----- is a single bond, and $CR_{2c}$ when ----- is a double bond, $R_1$ and $R_2$ are each independently a hydrogen atom; a halogen atom; a linear or branched, saturated or unsaturated hydrocarbon chain having from 1 to 10 carbon atoms; an optionally substituted aryl; or an optionally substituted heteroaryl, and wherein at least one of $R_1$ and $R_2$ is a linear or branched, saturated or unsaturated hydrocarbon chain having from 1 to 10 carbon atoms; an optionally substituted aryl; or an optionally substituted heteroaryl, $R_{1a}$ and $R_{2c}$ are each independently a hydrogen atom or a $(C_1$-$C_6)$alkyl group, and $R_{2a}$ and $R_{2b}$ are each independently a $(C_1$-$C_6)$alkyl group, comprising the following successive steps:

(a2) coupling of a compound of formula (I) as defined above wherein at least one of $R_1$ and $R_2$ is a halogen atom, with a boronic acid derivative of formula $R_3$—$B(R_4)_2$ or $R_3$—$BF_3^-K^+$ wherein $R_3$ is a linear or branched, saturated or unsaturated hydrocarbon chain having from 1 to 10 carbon atoms; an optionally substituted aryl; or an optionally substituted heteroaryl, and $R_4$ is a $(C_1$-$C_6)$ alkyl, OH or $(C_1$-$C_6)$alkoxy group, or with a zinc derivative of formula $R_3$—Zn-Hal wherein $R_3$ is as defined above and Hal is a halogen atom, or with a stannane derivative of formula $R_3$-$SnA_1A_2A_3$ wherein $R_3$ is as defined above and $A_1$, $A_2$ and $A_3$, which can be identical or different, are each a $(C_1$-$C_6)$ alkyl group, or with a magnesium derivative of formula $R_3$—Mg-Hal wherein $R_3$ and Hal are as defined above, or with a silicon derivative of formula $R_3$—$SiMe_2OH$, $R_3$—$SiF_3$ or $R_3$—$Si(OA_1)(OA_2)(OA_3)$ wherein $R_3$, $A_1$, $A_2$ and $A_3$ are as defined above, or with an alkyne of formula R'—C≡CH wherein R' is a protecting group or a linear or branched, saturated or unsaturated hydrocarbon chain having from 1 to 8 carbon atoms, (b2) when step (a2) was performed with an alkyne of formula R'—C≡CH wherein R' is a protecting group, deprotection of the protecting group of the alkyne function, and (c2) optionally salification and/or solvation of the compound of formula (I) obtained in the preceding step to give a pharmaceutically acceptable salt and/or solvate of the compound of formula (I).

15. The process according to claim 14, wherein at least one of $R_1$ and $R_2$ is Cl, Br or I and Hal is Cl, Br or I.

* * * * *

UNITED STATES PATENT AND TRADEMARK OFFICE
CERTIFICATE OF CORRECTION

PATENT NO. : 10,550,115 B2  
APPLICATION NO. : 15/767053  
DATED : February 4, 2020  
INVENTOR(S) : Bruno Figadere et al.

Page 1 of 1

It is certified that error appears in the above-identified patent and that said Letters Patent is hereby corrected as shown below:

In the Claims

Claim 12, Line 25, in which "CH=C-CR$_{2a}$R$_{2b}$Hal" should read -- CH≡C-CR$_{2a}$R$_{2b}$Hal --

Signed and Sealed this  
Thirteenth Day of April, 2021

Drew Hirshfeld  
*Performing the Functions and Duties of the*  
*Under Secretary of Commerce for Intellectual Property and*  
*Director of the United States Patent and Trademark Office*